United States Patent
Ghogawala

(10) Patent No.: US 10,937,552 B2
(45) Date of Patent: Mar. 2, 2021

(54) SYSTEMS AND METHODS FOR AN ONLINE MEDICAL PANEL

(71) Applicant: GN2.0-NIDUS, INC., Needham, MA (US)

(72) Inventor: Zoher Ghogawala, Needham, MA (US)

(73) Assignee: GN2.0-NIDUS, INC., Needham, MA (US)

(*) Notice: Subject to any disclaimer, the term of this patent is extended or adjusted under 35 U.S.C. 154(b) by 0 days.

(21) Appl. No.: 16/116,496

(22) Filed: Aug. 29, 2018

(65) Prior Publication Data
US 2019/0027257 A1   Jan. 24, 2019

Related U.S. Application Data

(63) Continuation of application No. PCT/US2017/055168, filed on Oct. 4, 2017.
(Continued)

(51) Int. Cl.
*G16H 80/00* (2018.01)
*G06Q 30/02* (2012.01)
(Continued)

(52) U.S. Cl.
CPC ......... *G16H 80/00* (2018.01); *G06Q 30/0201* (2013.01); *G16H 10/60* (2018.01);
(Continued)

(58) Field of Classification Search
CPC ........ G16H 10/60; G16H 40/67; G16H 80/00; G16H 15/00
(Continued)

(56) References Cited

U.S. PATENT DOCUMENTS

2001/0021910 A1* 9/2001 Goldstein ............. G06F 19/328
705/2
2002/0133374 A1* 9/2002 Agoni .................... G06Q 10/10
705/2

(Continued)

FOREIGN PATENT DOCUMENTS

WO   WO-2008091808 A2 *  7/2008  ............. G16H 50/20
WO   WO 2012148817       11/2012

OTHER PUBLICATIONS

Written Opinion for PCT/US17/055168 dated Jan. 2, 2018; 12 pps.
(Continued)

*Primary Examiner* — John P Go
(74) *Attorney, Agent, or Firm* — Nutter McClennen & Fish LLP

(57) ABSTRACT

In accordance with some embodiments, systems and methods provide for generating a panel of medical experts for a patient being treated by a treating physician who has been diagnosed with a medical condition, the panel of medical experts providing in a timely manner recommendations for a treatment plan for the patient's medical condition. In accordance with some embodiments, the treating physician submits an Opinion Request to an automated service that selects the panel of medical experts, the treating physician providing a narrative of the relevant medical history of the patient and relevant medical images for review by the panel. In accordance with some embodiments, a resultant report of the treatment recommendations from the panel is provided to the treating physician for dissemination to the patient.

15 Claims, 14 Drawing Sheets

Related U.S. Application Data

(60) Provisional application No. 62/403,949, filed on Oct. 4, 2016.

(51) Int. Cl.

| | | |
|---|---|---|
| *G16H 10/60* | (2018.01) | |
| *G16H 50/70* | (2018.01) | |
| *G16H 50/20* | (2018.01) | |
| *G06Q 50/22* | (2018.01) | |
| *G16H 30/00* | (2018.01) | |
| *G16H 20/10* | (2018.01) | |
| *G06F 21/62* | (2013.01) | |

(52) U.S. Cl.
 CPC .............. *G16H 50/20* (2018.01); *G16H 50/70* (2018.01); *G06F 21/6245* (2013.01); *G06F 2221/2141* (2013.01); *G06Q 50/22* (2013.01); *G16H 20/10* (2018.01); *G16H 30/00* (2018.01)

(58) Field of Classification Search
 USPC ........................................................ 705/2–4
 See application file for complete search history.

(56) References Cited

U.S. PATENT DOCUMENTS

| | | | | |
|---|---|---|---|---|
| 2002/0138304 A1* | 9/2002 | Fontanesi | .............. | G06Q 10/10 705/2 |
| 2003/0105773 A1* | 6/2003 | Linde | ...................... | G06Q 30/02 |
| 2004/0122701 A1* | 6/2004 | Dahlin | ................ | G01S 7/52098 705/2 |
| 2008/0262869 A1* | 10/2008 | Bronn | ................... | G06F 19/325 705/2 |
| 2008/0292159 A1* | 11/2008 | Soenksen | .............. | G06F 19/321 382/128 |
| 2009/0259492 A1* | 10/2009 | Cossman | .............. | G06F 19/328 705/3 |
| 2010/0138240 A1* | 6/2010 | Leib | ...................... | G06F 19/321 705/3 |
| 2011/0041173 A1 | 2/2011 | Kurtzig et al. | | |
| 2012/0016690 A1* | 1/2012 | Ramarajan | ............. | G16H 50/20 705/2 |
| 2012/0061669 A1 | 3/2012 | Kim et al. | | |
| 2012/0116800 A1* | 5/2012 | McCallie | .............. | G06F 19/325 705/2 |
| 2012/0245952 A1* | 9/2012 | Halterman | ............. | G16H 50/20 705/2 |
| 2014/0275807 A1* | 9/2014 | Redei | ................... | A61B 5/0022 600/300 |
| 2015/0006261 A1* | 1/2015 | Gutman | ................ | G06Q 50/22 705/7.39 |
| 2015/0073824 A1* | 3/2015 | Norris | ............... | G06F 16/24575 705/2 |
| 2015/0269316 A1* | 9/2015 | Hussam | ................ | G16H 10/60 705/3 |

OTHER PUBLICATIONS

International Search Report for PCT/US17/055168 dated Jan. 2, 2018; 2 pps.

Ghogawala, Zoher et al. "Laminectomy plus Fusion versus Laminenctomy Alone for Lumbar Spondylolisthesis" The New England Journal of Medicine; Apr. 14, 2016; pp. 1424-1434.

Ghogawala, Z., MD, et al. "Lumbar Spondylolisthesis: Modern Registries and the Development of Artificial Intelligence". JNS Spine Literature Review. vol. 30. Jun. 2019. pp. 729-735.

\* cited by examiner

Case Identifier: 1003726

Date Initiated: 06/13/2016

Narrative: 75-year-old female with neurogenic claudication and L3/L4 spondylolisthesis and L4/L5 spondylolisthesis with stenosis at L4-L5. Flexion-Extension x-rays demonstrate 3 mm movemnt at L4-L5 with flexion. There is 2mm motion with flexion at L3-L4. There is lateral recess and central canal stenosis at L4-L5. Sagittal MRI shows L3-L4 grade I spondylolisthesis. Flexion standing x-ray shows L3-L4 and L4-L5 spondylolisthesis.

Accompanying Files: Flexion X-Ray, Extension X-Ray, Sagittal MR, Axial MR, Axial MR

FIG. 3A

Case Identifier: 1003726

Summary of Results: 16 Surveys completed; 100% said yes to surgery assuming conservative approaches had failed. 10 recommend Laminectomy, 6 recommend Laminectomy with Fusion.

| Medical Expert Identifier | Approach | Comments |
|---|---|---|
| EB-4637 | Laminectomy & Foraminotomies alone | Decompress both L3-4 and L4-5 |
| SM-2736 | Laminectomy | L4-5 hemilaminectomy with bilateral lateral recess decompression |
| DS-9374 | Laminectomy with Fusion | Non-posterolateral fusion using local autografty |
| PM-2784 | Laminectomy with Fusion | L3-L5 TLIF |
| TA-9423 | Laminectomy with Fusion | Laminectomy L3-5 (preserve L5-S1 interspinous starting ant l45 interspace), Local and instrument plus/minus extender. No interbody |
| EB-8463 | Laminectomy with Fusion | L4-5 decompression with posterolateral fusion |
| AK-3372 | Laminectomy alone | Symptoms are claudification, not mechanical pain. At 75 y.o., I would perform a lami and possibly non-instrumental fusion, but no screws at initial sugery as slip is minimal and currently not symptomatic, and perhaps never will be given at her age. |
| PM-6632 | Laminectomy alone | Bilateral fenestration/ interlaminar laminotomy L4, L5 |

FIG. 3D

| | | |
|---|---|---|
| AF-7462 | Laminectomy | Hemilaminectomy of inferior portion of L3 and Hemilaminectomy L4 with bilateral decompression |
| VR-0473 | Laminectomy | If she has failed conservative therapy and symptoms are affecting her ADL; Laminectomy only because og Grade 1 listhesis with <3 mm movement |
| DP-3871 | Laminectomy with Fusion | Decompression and fusion L3-4 and L4-5TLIF |
| MW-7463 | Laminectomy | Probably hemilaminotomy (ipsi-contra) |
| JW-5391 | Laminectomy with Fusion | Open laminectomy with fusion of both levels with screws, TLIF |
| JC-8392 | Decompression alone unless severe mechanical lbp | 2 level slip with low degree facet hyperintensity and favorable facet angle |
| YK-6293 | Laminectomy | Fenestration, partial laminectomy (medial facetectomy) |
| ZO-0138 | Laminectomy | L3-L5 laminectomy; no fusion |

3 MONTH VISIT

WORK STATUS: _____

DATE OF RETURN TO PRE-OP WORKING CAPACITY ___/___/___

QUESTIONNAIRE SCORES

EQ-5D _____

ODI _____

[ASSIGN]

[COMPLETE]

6 MONTH VISIT

WORK STATUS: _____

DATE OF RETURN TO PRE-OP WORKING CAPACITY ___/___/___

QUESTIONNAIRE SCORES

EQ-5D _____

ODI _____

[ASSIGN]

| 1 YEAR VISIT |

WORK STATUS: ___

DATE OF RETURN TO PRE-OP WORKING CAPACITY __/__/__

36-INCH STANDING PLAIN X-RAY   SELECT

QUESTIONNAIRE SCORES

EQ-5D ___

ODI ___

NASS SATISFACTION SCALE ___

1 YEAR RADIOLOGY DATA SHEET (OPTIONAL)

Y N   WAS 1 YEAR RADIOGRAPHIC ASSESSMENT DONE?   [COMPLETE]

GENERAL FOLLOW-UP QUESTIONS

STATE YOUR OUTCOME ___

Y N   ARE YOU HAPPY WITH YOUR DECISION TO HAVE HAD SURGERY?

N Y   HAVE YOU HAD ANY FURTHER BACK SURGERY SINCE THE OPERATION?

FIG. 6B

SYSTEMS AND METHODS FOR AN ONLINE MEDICAL PANEL

CLAIM OF PRIORITY

The present application is a Continuation Application of PCT Application No. PCT/US17/055168, filed in the name of Zoher Ghogawala on Oct. 4, 2017 and titled SYSTEMS AND METHODS FOR AN ONLINE MEDICAL PANEL. PCT/US17/055168 claims the benefit of U.S. Provisional Application No. 62/403,949, filed on Oct. 4, 2016 and titled SYSTEMS AND METHODS FOR AN ONLINE MEDICAL DIAGNOSIS PANEL. The entirety of each of these applications is incorporated by reference herein for all purposes.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION(S)

Embodiments described herein relate to systems, methods and articles of manufacture for facilitating an online system via which panels of medical experts can recommend one or more treatment strategies to a doctor who is treating a patient.

BRIEF DESCRIPTION OF THE FIGURES

Features, aspects and advantages of various embodiments are described in detail below with reference to the accompanying drawings, which are intended to illustrate and not to limit the embodiments. The drawings comprise the following figures in which:

FIGS. 3A-3E comprise example embodiments of user interfaces that may be useful for facilitating one or more embodiments described herein, as they may be rendered in a web browser in accordance with some embodiments;

FIGS. 5A-5C comprise renderings of some example user interfaces that may be useful in at least some embodiments described herein;

FIGS. 6A and 6B comprise renderings of some example user interfaces that may be useful in at least some embodiments described herein.

DETAILED DESCRIPTION

Figure 1:
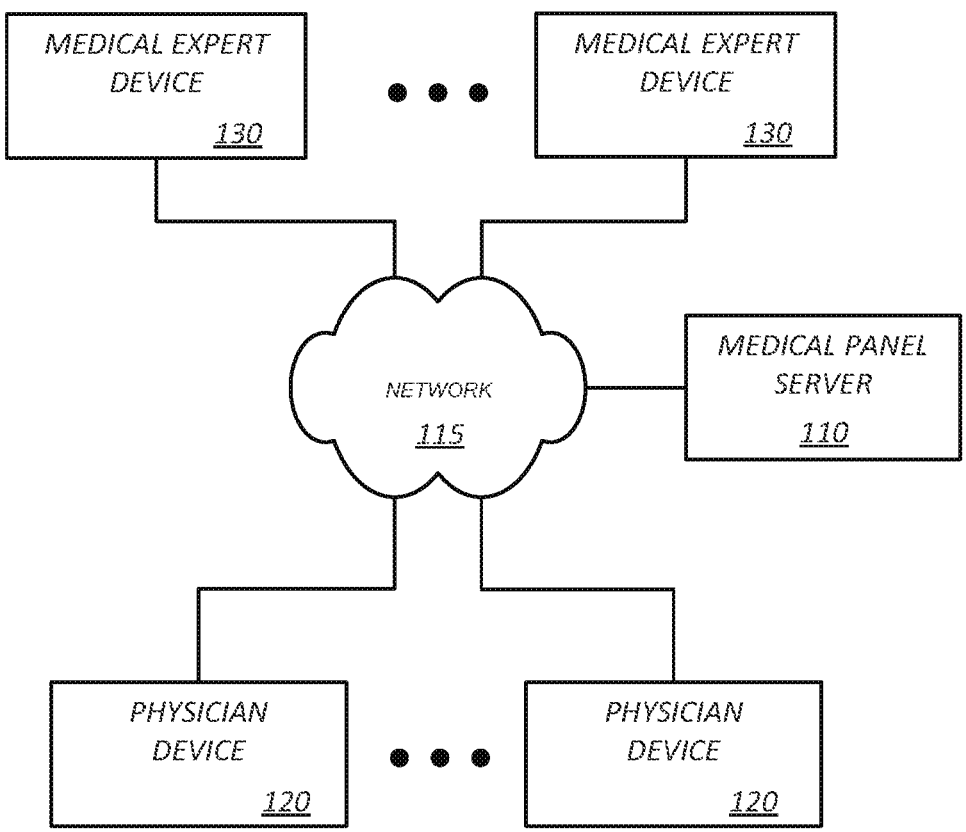
FIG. 1 is a schematic diagram of an embodiment of a system in accordance with one or more embodiments described herein.

Applicant has recognized that patients who are facing different treatment options for a medical condition often would prefer additional information from medical professionals with skill and expertise in the relevant area of medicine. For example, a patient experiencing discomfort or pain with their spine who is facing a choice between laminectomy alone or laminectomy with fusion is likely to be confused about whether their personal physician's recommendation for one choice over the other is a fair representation of what other physicians would recommend for his/her condition. In another example, a cancer patient faced with deciding between chemotherapy and radiation would probably feel more comfortable making the choice after consulting more than one oncologist. Applicant has further recognized that physicians would prefer to have their patients be more comfortable accepting their recommendations and seek ways to allow their patients to become more informed in a credible manner (e.g., information a patient may find online on his/her own may not always be credible from the physician's perspective, nor would it be tailored to the patient's particular medical situation).

Applicant has recognized that although both a patient and his treating physician would benefit from the patient being more comfortable and informed regarding the physician's recommended treatment options, there are currently few viable mechanisms for the patient to obtain this information. As one potential available solution, a patient can seek second or third opinions from other doctors who specialize in the medical condition of the patient. This, however, places several burdens on the patient. First, the patient has to take the time to make and keep yet another doctor's appointment, obtain his current physical records and make sure the new doctor is provided with the relevant condition (or go through a second set of duplicate examinations and tests so the new doctor can obtain this information independently). Second, sometimes the patient's insurance will not cover duplicate doctor visits and/or tests for the same condition and, even if the insurance policy would cover such visits and/or test, the patient may have a deductible that would result in extra out-of-pocket costs for the patient in pursuing additional opinions from additional physicians. Further, given the limited time and financial resources of a patient, it is only realistic for the patient to seek at most two additional opinions for his/her condition, which may not be sufficient for the patient to achieve a satisfactory comfort level when deciding on a treatment option. As yet another obstacle, given the expenses and time of travel, the patient is typically limited to seeking additional opinions from physicians who are within close geographical proximity to the patient (e.g., reasonable driving distance for a one-day visit).

Another currently available option for a patient seeking additional opinions when deciding on medical treatment options is to research the options online. Given the volume of information available online, however, as well as the questionable credibility of some sources, many patients and physicians do not feel comfortable relying significantly on research the patient may do online. Seeking a general understanding of the different medical treatment options and the general pros and cons of each may be helpful, but it does not address the patient's concerns regarding which treatment option is best for him/her given the particular context of the patient (medical history, demographics, financial constraints, etc.). Unfortunately, often a patient will not even be aware of what facts or data would be most relevant to a qualified physician in recommending which of a plurality of treatment options the patient should pursue.

Finally, there are currently some online diagnostics services that allow physicians to diagnose a patient remotely. These services, however, are not equipped to provide diagnosis and treatment recommendations for complex medical conditions such as lumbar spondylolisthesis or cancer. Rather, they are geared towards providing patients with more common ailments (e.g., cold, flu, sinus infection) easier access to basic medical care. Most physicians who treat more complex medical conditions require data and information (e.g., CT Scans, X-Rays, patient medical background and relevant demographic information) that a patient may not be equipped to provide or have available in his/her records. Further, such online diagnosis tools provide an external second opinion, much like seeking a second opinion from another physician, that occurs outside the treating physician-patient relationship and is thus not as effective in helping a treating physician and his/her patient decide on the best treatment option for the patient in a collaborative fashion.

Applicant has recognized that patients typically prefer to maintain their relationship with the physician who is treating them and are not seeking to replace this relationship with an online diagnostics tool or another live physician but are rather seeking to supplement their physician's recommendations of treatment options with additional information and opinions regarding the available treatment options. Applicant believes that the desire of a patient for reassurance or corroboration of treatment options or a physician's recommendations would best be satisfied if done within the context of the treating physician-patient relationship so that both the treating physician and the patient can together obtain, review and incorporate the additional information into the patient's treatment plan. Applicant further believes that an effective solution for providing to a patient additional opinions from one or more qualified physicians would also help strengthen the treating physician-relationship and the physician's comfort level with the treatment option that is settled upon for his/her patient.

In accordance with some embodiments, systems, methods and articles of manufacture (e.g., non-transitory, computer-readable media) may provide for: (i) receiving, from a treating physician, data relevant to a patient's medical condition; (ii) generating, based at least on the data, a panel of a plurality of medical experts that are qualified to treat the medical condition; (iii) forward information, based on the data, to each of the medical experts comprising the panel; (iv) receive, from each of the medical experts, a recommended treatment option for the medical condition as it applies to the patient based on the information, thereby receiving a plurality of recommendations from the panel; and (v) generating a report for the treating physician, the report summarizing the recommendations. Thus, in accordance with at least some embodiments, a treating physician is able to request and obtain, for his/her patient, a report that indicates how a plurality of other medical experts who are qualified to treat the patient's medical condition would treat the patient's medical condition. The request for medical opinions or other input relevant to the medical condition, diagnosis and/or treatment options with respect to a particular patient and from a particular treating physician is referred to as an Opinion Request herein. In accordance with some embodiments, a system may be operable to receive an Opinion Request from a treating physician, generate a panel of medical experts with expertise in a field relevant to the patient's medical condition (e.g., 5-20 experts, which provides significantly more "second" opinions to a patient than the patient could reasonably obtain on his/her own) and transmit to each medical expert on the medical panel information relevant to the requested medical opinion based on the Opinion Request (e.g., a summary of the patient's medical conditions and relevant history, medical files, etc.). In some embodiments, the information provided to a medical expert may be referred to herein as an Opinion Request, even if it is not exactly the same or all of the information provided by a treating physician when submitting an Opinion Request (e.g., information may be redacted, added or re-formatted to the Opinion Request as it is received from a treating physician prior to being forwarded to a medical expert on a medical panel assigned to the Opinion Request).

In accordance with some embodiments, each medical expert on a medical panel assigned to an Opinion Request is prompted by the system to provide an opinion as to how the patient's medical condition should be treated and/or a medical diagnosis for the patient's medical condition. In one example, a medical expert may be given a plurality of choices from which to choose or some other pre-formatted selection of choices from which to choose in providing such opinion. In another embodiment, a medical expert may be prompted to provide an opinion in free-form (e.g., without selecting from pre-formatted options, such as by typing text into a text box). In still other embodiments, the medical expert may be prompted to provide a combination of inputs when responding to an Opinion Request (e.g., select one or more options from a menu of available options regarding treatment options and/or diagnosis and write any notes the medical expert desires to have considered with his opinion). A resulting summary or other information indicating the inputs, responses and/or selected choices (i.e., the medical opinions regarding a recommended treatment plan and/or diagnosis for a given patient) as received from medical experts comprising a medical panel and for a particular Opinion Request is referred to as an Opinion Report herein. In accordance with some embodiments, an Opinion Report is provided to a treating physician in response to an Opinion Request and the treating physician may then share such Opinion Report with the patient who is the subject of the Opinion Request. In accordance with some embodiments, an Opinion Request is provided to a treating physician within a relatively short timeframe from the Opinion Request having been received by the system (e.g., within 48 hours or within two weeks), a timeframe that would not be reasonably satisfied if the patient were to physically try to visit the same or event close to the same number of medical experts to seek second opinions in a traditional manner (e.g., find out which medical experts within a reasonable travel range are within the patient's insurance network, make appointments to visit the medical experts, undergo a time consuming visit and potentially additional testing or imaging, etc.). Accordingly, the systems and methods described herein provide a heretofore unavailable option of providing to a patient, within a few days of a request for such and without the patient having to find (much less make appointments with and visit) additional medical experts, a plurality of second opinions regarding recommended treatment options. The systems and methods have the ability to further provide to the patient second opinions from medical experts who may be located very far away from the patient (e.g., in another state, country or even continent), which medical experts may not otherwise be reasonably accessible to the patient. Further, the systems and methods described herein generate Opinion Requests which include pertinent medical data that can easily be uploaded by a patient's treating physician (biopsy results, key MM image, x-ray). This removes the burden for patients who would may not have a reasonable ability to identify, much less access, such specific elements of their medical records and provide them to a medical expert from whom they are seeking a second opinion, much less to do so via an online process. The solution further simplifies the process for medical experts who are asked to provide second opinions on recommended treatment options, by focusing the medical expert on the key elements of the medical history that are relevant for the diagnosis and treatment plan and providing a mechanism via which the relevant data files (e.g., relevant radiographs) are provided to the medical experts along with the Opinion Request.

An Opinion Report in accordance with at least some embodiments described herein allows a treating physician, within the context of the physician-patient relationship, to provide additional information and assurance to the patient as to whether the treating physician's recommended treatment option is supported by the opinions of a plurality of other qualified medical experts. The patient is able to enjoy the benefits of such a report (e.g., reassurance that the treatment option being recommended by his treating physician is supported by other physicians) without having to go to the trouble or expense of finding a qualified medical expert (much less a plurality of qualified medical experts), obtaining and providing the relevant medical data about his/her medical condition to the additional medical expert (s), subjecting him/herself to another doctor visit and the attendant time and expenses that may be associated with such visits, and doing so with the support and collaboration of his treating physician (which Applicant believes helps strengthen the trust and relationship between the treating physician and patient). Additionally, the system in accordance with at least some embodiments is able to provide such recommendations and attendant Opinion Report in a manner that includes opinions from medical experts who may not otherwise be accessible to the patient (e.g., medical experts from top medical institutions who may not have available time for new patient visits but who do have the time to review the patient's data and provide an opinion and/or medical experts who are geographically distant from the patient's area of residence). Also, the system provides the treating physician with either reassurance that his recommended treatment option is supported by other experts in his/her field or an opportunity to receive a recommendation for a different treatment option and perhaps be persuaded to change his original recommendation, follow-up with an expert who recommended a different or unexpected treatment option or a comment that leads the treating physician to consider one or more factors (or perhaps new results, data or studies in a relevant field) he/she may not previously have considered, and grow his knowledge and comfort level in his/her field.

Certain aspects, advantages, and novel features of various embodiments are described herein. It is to be understood that not necessarily all such advantages may be achieved in accordance with any particular embodiment of the invention (s) described. Thus, for example, those skilled in the art will recognize that embodiments described herein may be embodied or carried out in a manner that achieves one advantage or group of advantages as taught herein without necessarily achieving other advantages as may be taught or suggested herein.

Although several embodiments, examples and illustrations are disclosed below, it will be understood by those of ordinary skill in the art that the invention(s) described herein extend(s) beyond the specifically disclosed embodiments, examples and illustrations and includes other uses of the invention(s) and obvious modifications and equivalents thereof. Embodiments of the invention(s) are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention (s). In addition, embodiments of the invention(s) can comprise several novel features and it is possible that no single feature is solely responsible for its desirable attributes or is essential to practicing the invention(s) herein described.

Referring now to FIG. 1, illustrated therein is an example system 100 consistent with one or more embodiments. The system 100 comprises a Medical Panel Server 110, a plurality of Physician Devices 120 and a plurality of Medical Expert Devices 130. The system 100 is one example embodiment of a system which may be operable to facilitate at least some embodiments described herein. In other words, the system 100 may be useful in facilitating a medical panel service provider (e.g., which may operate the Medical Panel Server 110) in providing various tools and resources to allow a physician who is treating a patient to obtain second opinions, medical diagnoses and/or treatment recommendations from medical experts (e.g., other physicians who specialize in the disease or medical condition that is ailing the patient) in order to provide additional information on treatment options to the patient.

In some embodiments, one or more of these User Devices 120 and/or Medical Expert Device 130 may be operable to communicate with Medical Panel Server 110 via a network 115. The network 115 may comprise, for example, a mobile network such as a cellular, satellite or pager network, the Internet, a wide area network, another network or a combination of such networks. It should be understood that although not shown in FIG. 1, other networks and devices may be in communication with any of the devices of system 100 and/or that network 115 may comprise two or more networks operable to facilitate the routing of communications among the devices of system 100. For example, in one embodiment, both the Internet and a wireless cellular network may be involved in routing communications among two or more components of the system 100.

In some embodiments, additional devices that are not shown in FIG. 1 may be part of a system 100. For example, one or more servers operable to serve as wireless network gateways or routers may be part of system 100. In other embodiments, some of the functionality described herein as being performed by Medical Panel Server 110 may instead or in addition be performed by a server of another entity operating on behalf of the Medical Panel Server 110 (e.g., the entity that operates or controls the services provided via Medical Panel Server 110 may outsource some functionality or otherwise allow some functionality to be performed by servers of other entities, such as registration of new medical experts and/or physicians, storing or facilitating the sharing of medical files, authorization of transactions, etc.). In one example, if a physician or an agent of a physician uploads one or more medical files of a patient for use in requesting feedback on the patient's diagnosis or recommended medical treatment from a panel of medical experts, such medical file may be stored on a server of another entity and be accessible by Medical Panel Server 110. Thus, a server of another entity may be a part of system 100 or otherwise be operable to communicate with Medical Panel Server 110. It should be understood that any of the functionality described herein as being performed by the Medical Panel Server 110 may in some embodiments be performed by such server of another entity.

The Medical Panel Server 110 may comprise one or more computing devices, working in parallel or series if more than one, operable to facilitate a physician's request to obtain feedback or input from a panel of relevant medical experts regarding a patient's medical diagnosis or recommended medical treatment. The Medical Panel Server 110 may be operated by or on behalf of an entity which offers services to facilitate such efforts of various users on behalf of one or more organizations in accordance with embodiments described herein. As described herein, the Medical Panel Server 110 may be operable, in accordance with some embodiments, to (i) communicate with a Physician Device 120 (e.g., receive login credentials from the Physician Device, receive a selection of information for use in requesting input from a panel of medical experts regarding a patient's medical diagnosis or recommended medical treatment, etc.); (ii) receive information regarding medical experts who desire to participate in medical panels generated by the system (e.g., education, certifications, credentials, areas of expertise, peer verifications or reviews, employment history, peer-reviewed publications etc.); (iii) select available medical experts to form a panel for a particular request from a physician and facilitate communications with the members of the panel; (iv) generate a panel of medical experts for a particular Opinion Request (e.g., by selecting the desired number of experts based on credentials, area of expertise, availability, history of participation in previous panels, etc.); (v) receive input from a medical expert in response to an Opinion Request (i.e., a response from a medical expert that indicates at least one recommended medical treatment, medical opinion and/or explains any assumptions or considerations the providing medical expert considers relevant to the recommended treatment and/or medical opinion); and/or (vi) generate a report or summary of the inputs received from the medical experts comprising a panel for a particular Opinion Request.

A Physician Device 120 may comprise a computing device associated with a physician utilizing the services of the Medical Panel Server 110. For example, a Physician Device 120 may comprise a personal computer such as a desktop, laptop or tablet computer, a cellular telephone or a smartphone or other mobile device. A Physician Device 120 may be operable, in accordance with some embodiments, communicate with the Medical Panel Server 110 to allow a treating physician (or an agent thereof, such as a nurse or administrative assistant of the treating physician) to log in to the Medical Panel Server 110 (e.g., to register to participate in the services of the Medical Panel Server 110, submit an Opinion Request, upload data such as medical files that support an Opinion Request, access and print an Opinion Report, etc.).

A Medical Expert Device 130 may comprise one or more computing devices, working in parallel or series if more than one, that may be operated by a medical expert (e.g., a physician or other medical expert who has registered with the Medical Panel Server 110 or the entity operating the foregoing as one who is willing to be included on medical panels to which Opinion Requests are provided on behalf of a treating physician). A Medical Expert Device 130 may be operable to transmit information to or receive information from the Medical Panel Server 110. Such information may comprise, for example, information relevant to a medical expert's expertise or credentials (e.g., educational background, peer recommendations, employment history, degrees or certifications earned, professional accreditations, peer-reviewed publications, etc.). In another example, such information may comprise rules or preferences of the medical expert to be applied by the Medical Panel Server 110 when determining whether to include the medical expert in a particular medical panel being generated for an Opinion Request (e.g., a frequency with which the medical expert wants to receive Opinion Requests, a maximum number of Opinion Requests the medical expert is willing to receive in a specified period of time (e.g., per month), a compensation or remuneration the medical expert prefers to receive in exchange for participating in medical panels (in embodiments in which compensation or remuneration is provided or in which the medical expert has a choice with respect to the foregoing).

It should be noted that whenever information is described as being "transmitted" to a device of system 100 or other systems described herein, it is intended to encompass both a "push" embodiment in which the information is proactively pushed or output to the device by another device and a "pull" embodiment in which the device contacts another device in order to query for any updated information or changes in information.

In some embodiments, any of the components 110, 120 and 130 may communicate with one another directly or indirectly, via a wired or wireless medium such as the Internet, LAN, WAN or Ethernet, Token Ring, or via any appropriate communications means or combination of communications means. For example, in one embodiment communication among any and all of the devices of system 100 may occur over the Internet through a Web site maintained by computer on a remote server or over an on-line data network including commercial on-line service providers, bulletin board systems and the like. In some embodiments, communication among any of the components of system 100 may occur over radio signals, cellular networks, cable network, satellite links and the like.

The system 100 may be operable to facilitate communication using known communication protocols. Possible communication protocols that may be useful in the system 100 include, but are not limited to: Ethernet (or IEEE 802.3), ATP, BLUETOOTH, SMPP Protocol (e.g., SMPP Protocol Version 3.4), HTTP, HTTPS, and Transmission Control Protocol/Internet Protocol (TCP/IP). Communications may be encrypted to ensure privacy and prevent fraud in any of a variety of ways well known in the art, some of which are described herein.

It should be understood that any or all of the devices of system 100 may in some embodiments comprise one or more of (i) an input device; (ii) an output device; (iii) an input/output device; or (iv) a combination thereof.

An input device, as the term is used herein, may be any device, element or component (or combination thereof) that is capable of receiving an input (e.g., from a user or another device). An input device may communicate with or be part of another device. Some examples of input devices include: a bar-code scanner, a magnetic stripe reader, a computer keyboard or keypad, a button (e.g., mechanical, electromechanical or "soft", as in a portion of a touch-screen), a handle, a keypad, a touch-screen, a microphone, an infrared sensor, a voice recognition module, a coin or bill acceptor, a sonic ranger, a computer port, a video camera, a motion detector, a digital camera, a network card, a universal serial bus (USB) port, a GPS receiver, a radio frequency identification (RFID) receiver, an RF receiver, a thermometer, a pressure sensor, an infrared port, and a weight scale.

An output device may comprise any device, component or element (or a combination thereof) operable to output information from any of the devices described herein. Examples of an output device include, but are not limited to, a display (e.g., in the form of a touch screen), an audio speaker, an infra-red transmitter, a radio transmitter, an electric motor, a dispenser, an infra-red port, a Braille computer monitor, and a coin or bill dispenser.

An input/output device may comprise components capable of facilitating both input and output functions. In one example, a touch-sensitive display screen comprises an input/output device (e.g., the device outputs graphics and receives selections from an authorized person).

Figure 2:
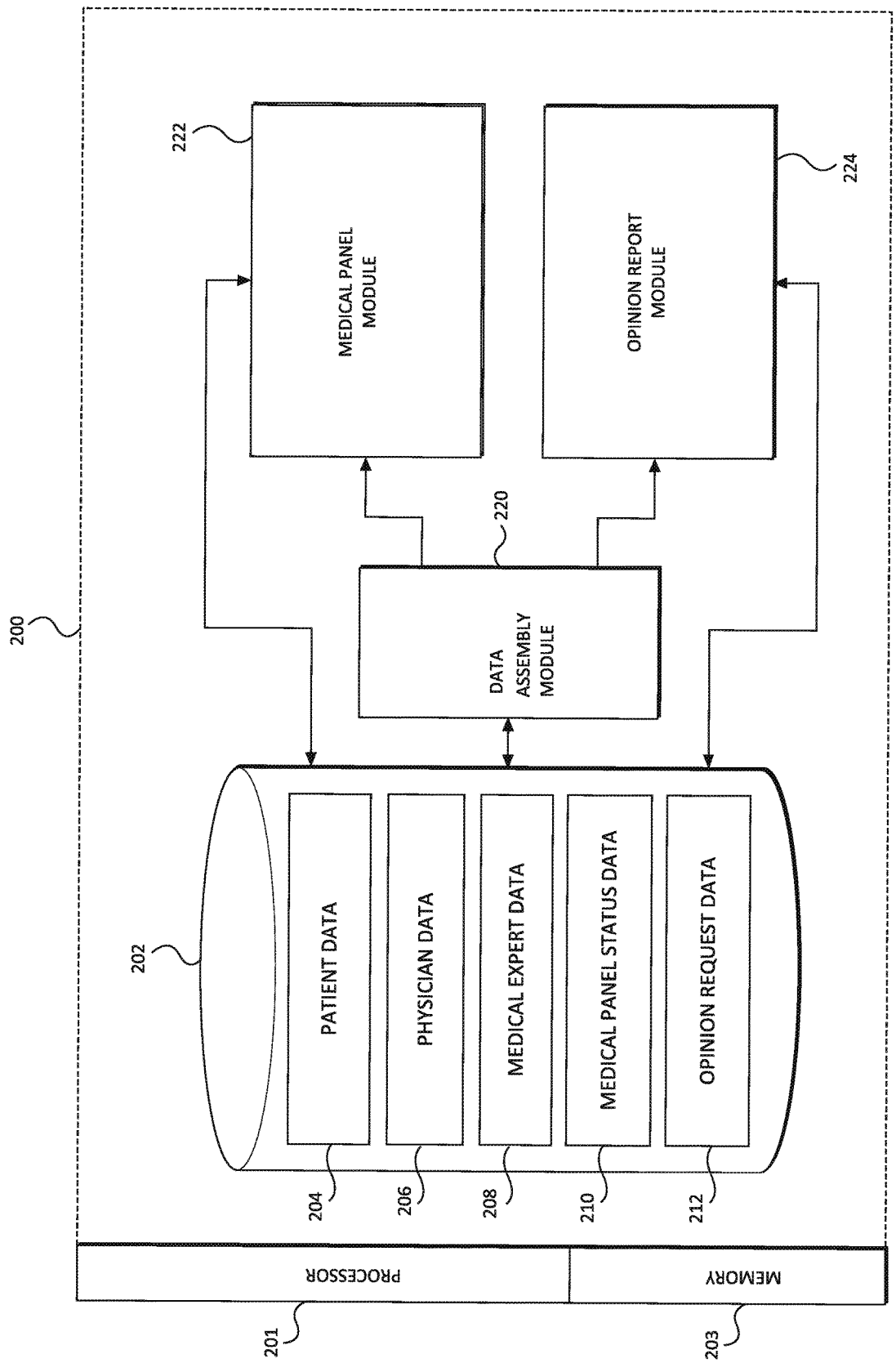
FIG. 2 is a block diagram of an embodiment of a computing device useful in a system according to one or more embodiments described herein.

Referring now to FIG. 2, illustrated therein is a computer system 200, which may be useful for implementing one or more embodiments described herein. For example, the computer system 200 may, according to some embodiments, be configured to select medical experts to form a panel responsive to an Opinion Request received from a treating physician and output information to each of the medical experts comprising the panel to enable each expert to provide an opinion for the Opinion Request (e.g., the computer system 200 may output to a medical expert a brief description of relevant patient medical and/or demographic information as well as one or more medical files such as X-Ray or other images). In some embodiments, the computer system 200 may apply an algorithm (e.g., a propensity score, as described herein) and/or one or more rules for selecting the particular medical experts to form a particular panel for a particular Opinion Request.

The system 200 may be implemented using one or more processors, such as processor 201, in conjunction with one or more tangible computer readable storage medium devices, such as memory device 203. The operations described herein may be divided across a plurality of computing systems, and are shown to reside in a single processing device of FIG. 2 so as to simplify the description. The computer system 200 may, for example, be operated by or on behalf of an entity which facilitates a treating physician obtaining an Opinion Report that summarizes a plurality of medical opinions from a plurality of qualified medical experts in a timely manner (e.g., within one to seven days) for a patient of the treating physician. The computer system 200 may do so by communicating with (i) one or more medical experts and (ii) the treating physician and/or an agent thereof. In one embodiment, system 200 may comprise the Medical Panel Server 110 of system 100 (FIG. 1).

In some embodiments, additional devices or components that are not shown in FIG. 2 may be part of a system for facilitating Opinion Reports as described herein. For example, one or more servers operable to serve as wireless network gateways or routers may be part of such a system. In other embodiments, some of the functionality described herein as being performed by system 200 may alternatively or in addition be performed by a third party server operating on behalf of the system 200 (e.g., the entity operating the Medical Panel Server 110 may outsource some functionality, such as registration of new users, uploading or otherwise obtaining relevant medical files of a patient, collecting of payments or outputting of messages or notifications to users). Thus, a third party server may be a part of a system, such as that illustrated in FIG. 2. It should be understood that any of the functionality described herein as being performed by the system 200 may in some embodiments be performed by such a third party server. For example, one or more of the functions or processes described herein as being performed by system 200 or a component thereof (e.g., a module or software application of system 200) may be implemented with the use of one or more cloud-based servers which, in one embodiment, may be operated by or with the help of a third party distinct from the entity from which treating physicians obtain Opinion Reports or to which treating physicians submit Opinion Requests. In other words, while in some embodiments the computerized system 200 may be implemented on servers that are maintained by or on behalf of a particular company or business which helps facilitate Opinion Requests and/or Opinion Reports, in other embodiments the system 200 may at least partially be implemented using other arrangements, such as in a cloud-computing environment, for example.

The computer system shown in the embodiment of FIG. 2 includes a database 202, which may store one or more of the following: (i) patient data records 204, which may include information and files regarding patients who are subjects of Opinion Request (e.g., demographic information, medical images or other files, associated treating physician, etc.); (ii) physician data records 206, which may include information regarding physicians who utilize the services facilitated by computer system 200 to obtain Opinion Reports for their patients (unique physician identifier, contact information, associated patients, history of Opinion Requests submitted and Opinion Reports received, etc.); (iii) medical expert data records 208, which may include information regarding medical experts who have registered with the system and agreed to provide medical opinions in response to Opinion Requests (e.g., area of expertise, professional credentials, associated hospital or employer, medical panels previous assigned to, peer reviews, patient and/or physician feedback or reviews, CV, etc.); (iv) medical panel status data records 210, which may include information regarding medical panels that have been created by the system and the status of such medical panels (e.g., which medical experts are included in a particular medical panel, which medical experts on a panel have already provided an opinion for a particular Opinion Request and which the system is still waiting on, etc.); and (v) opinion request data records 212, which may include information regarding Opinion Requests submitted by physicians (e.g., a unique Opinion Request identifier, the description of the patient's condition as submitted by the physician when submitting an Opinion Request, an identifier of a medical panel and/or one or more medical experts assigned to the Opinion Request, a status of responses and/or corresponding Opinion Report, etc.).

The database 202 may, for example, be implemented using any well-known database management systems, including Microsoft SQL, Oracle, IBM DB2, etc. It should be noted that in some embodiments, database 202 (or at least some of the data described as being stored therein) may be stored in memory 203 and/or in another memory device accessible to the memory 203 and/or to processor 201. For example, in one embodiment database 202 (or at least some of the data described as being stored therein) may be stored in a memory of a third party server, such as a server of a cloud-based computing service with which a company (e.g., a company which facilitates the storage, sharing and/or downloading of medical files of patients) may contract for purposes of storing data.

In accordance with some embodiments, the system 200 may further comprise one or more modules, programs, or processor instructions for performing at least some of the functionalities described herein. In the example embodiment of FIG. 2, the system 200 may further comprise one or more software module(s) 220-224 for directing the processor 201 to perform certain functions. In accordance with some embodiments, software components, applications, routines or sub-routines, or sets of instructions for causing one or more processors to perform certain functions may be referred to as "modules". It should be noted that such modules, or any software or computer program referred to herein, may be written in any computer language and may be a portion of a monolithic code base, or may be developed in more discrete code portions, such as is typical in object-oriented computer languages. In addition, the modules, or any software or computer program referred to herein, may in some embodiments be distributed across a plurality of computer platforms, servers, terminals, and the like. For example, a given module may be implemented such that the described functions are performed by separate processors and/or computing hardware platforms. Further, although certain functionality may be described as being performed by a particular module, such description should not be taken in a limiting fashion. In other embodiments, functionality described herein as being performed by a particular module may instead (or additionally) be performed by a different module, program, sub-routine or computing device without departing from the spirit and scope of the invention(s) described herein.

It should be understood that any of the software module(s) or computer programs illustrated therein may be part of a single program or integrated into various programs for controlling processor 101. Further, any of the software module(s) or computer programs illustrated therein may be stored in a compressed, uncompiled, and/or encrypted format and include instructions which, when performed by the processor 201, cause the processor 101 to operate in accordance with at least some of the methods described herein. Of course, additional and/or different software module(s) or computer programs may be included and it should be understood that the example software module(s) illustrated and described with respect to FIG. 1 are not necessary in any embodiments. Use of the term "module" is not intended to imply that the functionality described with reference thereto is embodied as a stand-alone or independently functioning program or application. While in some embodiments functionality described with respect to a particular module may be independently functioning, in other embodiments such functionality is described with reference to a particular module for ease or convenience of description only and such functionality may in fact be a part of, integrated into, another module, program, application, or set of instructions for directing a processor of a computing device.

According to an embodiment, the instructions of any or all of the software module(s) or programs described with respect to FIG. 2 may be read into a main memory from another computer-readable medium, such from a ROM to RAM. Execution of sequences of the instructions in the software module(s) or programs causes processor 201 to perform at least some of the process steps or functionalities described herein. In alternate embodiments, hard-wired circuitry may be used in place of, or in combination with, software instructions for implementation of the processes of the embodiments described herein. Thus, the embodiments described herein are not limited to any specific combination of hardware and software.

In the example embodiment illustrated in FIG. 2, a data assembly module 220 is illustrated as communicating with (i) the memory 202, (ii) a data assembly module 220, (iii) a medical panel module 222 and (iii) an opinion report module 224. The modules 220-224 are illustrated as being accessible to processor 201 to implement one or more embodiments described herein. As described, one or more of the modules 220, 222 and 224 may be operable to utilize at least some of the data stored in database 202. Further, in accordance with some embodiments, one or more of the modules 220, 222 and 224 may be operable to retrieve, manipulate, select, and/or otherwise determine data that is transmitted to and stored in database 202.

Data assembly module 220 may, in accordance with some embodiments, operate to manipulate the data from database 202 into appropriate records for processing by the medical panel module 222 and/or by the opinion report module 224. For example, data assembly module 220 may be operable to provide information relevant to forming a medical panel for a new Opinion Request received by the system, based on some of data stored in a first record or entry of database 202 (e.g., based on data in the patient data records 204, the medical expert data records 208 and the opinion request data records 212), and transmit data comprising the medical panel for storage in another record or entry in the database 202 (e.g., for entry in medical panel status data records 210) and/or to transmit such data for use by medical panel module 222 (e.g., such that the medical panel module 222 may contact the medical experts comprising the panel and forward relevant information to them in seeking a medical opinion from them) and opinion report module 224 (e.g., for generating a report that indicates the medical opinion of each medical expert on a given medical panel).

In accordance with some embodiments, the medical panel module 222 may be operable to create and facilitate the putting together of medical panels for received Opinion Requests using at least some data stored in memory 202. For example, in one embodiment, the medical panel module 222 may be operable to utilize one or more rules or algorithms when selecting the particular medical experts to include in a panel being created in response to an Opinion Request having been received by the system from a treating physician. In one embodiment, the system may utilize general rules and/or algorithms to select medical experts for panels. Such rules or algorithms may take into account various factors, such as how many panels an expert has been placed on within a particular time frame, in order to load balance the number of Opinion Requests that are forwarded to a given medical expert within a particular time frame, the expertise or credentials of available experts and/or feedback or reviews from patients and/or treating physicians. In some embodiments, a propensity score may be generated for each potential or available medical expert and medical experts may be selected for a medical panel based on such propensity scores. In some embodiments, medical experts may set certain preferences or parameters for use by the system in determining whether to place a given medical expert on a medical panel (e.g., a maximum number of Opinion Requests the medical expert is willing to respond to in a given time period). Such preferences or parameters may be stored, for example, in medical expert data records 208 and the medical panel module 222 may utilize such preferences or parameters when creating a panel.

In accordance with some embodiments, medical panels are composed of individuals with recognized expertise in the field relevant to a given Opinion Request. For example, a medical expert being considered for a medical panel responsive to a particular Opinion Request may have published multiple peer-reviewed articles demonstrating their globally recognized expertise in a field relevant to the medical condition of the patient who is the subject of the Opinion Request for which a medical panel is being formed.

In accordance with some embodiments, medical panels may comprise groups of 10-15 medical experts. The particular number of medical experts on a given panel may vary depending on various factors, such as the clinical problem or medical condition involved, the number of medical experts available to serve on a given panel and/or the number of medical experts requested in a Opinion Request (in embodiments in which a treating physician is provided a choice in such number). In some embodiments a treating physician or patient (or the medical institution with which (s)he is affiliated) may provide a payment to the system for Opinion Requests/Reports (e.g., per Request/Report or on a subscription basis that may have a maximum number of such Requests/Reports per month or other timeframe). In such embodiments, there may be different tiers or categories of Opinion Requests/Reports available from the system, with the number of medical experts on a given panel dependent on the category of Opinion Request/Report involved. In some embodiments, additional medical experts may be added to a given medical panel if it appears that, after a certain number or percentage of responses from the initial medical panel have been received, there is no clear consensus or majority of experts that agree on a given treatment option or diagnosis. The embodiments described herein are not dependent on any particular number of medical experts on a medical panel.

In accordance with some embodiments, medical experts may be selected for a given panel based at least in part on a propensity score generated and updated by the system for the respective medical experts over time. In some embodiments, a propensity score may be reflective of a given medical expert's propensity to vote for or choose a particular treatment option over other treatment options for a given medical condition. For example, in one embodiment each medical expert's propensity scores for voting for one treatment option or another may be recorded and updated (e.g., in real time or periodically) as the medical expert participates in different medical panels. In one embodiment, a medical panel may thus be created for a given Opinion Request by selecting medical experts (e.g., randomly or based on an algorithm that seeks to achieve certain goals, such as a balance of propensity scores among the selected experts) for a given panel from among experts whose propensity for voting for particular medical treatment options is known.

In accordance with some embodiments, a propensity score may be anywhere between "0" and "1." In accordance with some embodiments, the system may be programmed to create a medical panel by selecting medical experts (e.g., based on availability and expertise, as described herein) based partly on the propensity scores of the potential medical experts such that, as a group, the resulting medical panel has an average propensity score for voting for or recommending one treatment option versus another in a desired range (e.g., between 0.4 and 0.6). Below is one example of how medical experts may be selected to serve on a given panel being generated for a particular Opinion Request based on propensity scores stored in the system for each medical expert.

Example A

For a clinical problem called cervical spondylotic myelopathy, surgeons either operate from the front or the back depending on patient anatomy. There is uncertainty around the optimal treatment for many patients. A medical panel has been created whose average propensity for voting for a front strategy is 43.3%. Therefore, the average propensity for voting for a 'back' strategy is 56.7%. There are two possible 'back' strategies and the overall propensity is divided roughly equally for the panel as a whole. Table 1 below summarizes the propensity scores compiled by the system for each of the medical experts selected for the panel (e.g., as determined based on each respective expert's selections when participating in previous medical panels), the average propensity scores for the panel (which is within the desired range of 0.4 and 0.6, in accordance with one embodiment). It should be noted that a medical panel identifier and an Opinion Request identifier may be generated by the system and assigned to each, in accordance with some embodiments.

TABLE 1

| Medical Panel ID: MP-74-2910-29 | | | Opinion Request ID: OP-10012016-8473 | |
|---|---|---|---|---|
| Medical Expert Identifier | % ventral | % dorsal | % lamifusion of dorsal | % laminoplasty of dorsal |
| ME-473829 | 0.629139 | 0.370861 | 0.232143 | 0.75 |
| ME-827222 | 0.227848 | 0.772152 | 0.188525 | 0.811475 |
| ME-748931 | 0.510791 | 0.489209 | 0.411765 | 0.573529 |
| ME-120382 | 0.210191 | 0.789809 | 0.435484 | 0.540323 |
| ME-748392 | 0.592308 | 0.407692 | 0.943396 | 0.056604 |
| ME-101923 | 0.358491 | 0.641509 | 0.362745 | 0.627451 |
| ME-578392 | 0.45 | 0.55 | 0.988636 | 0.011364 |
| ME-777321 | 0.392157 | 0.607843 | 0.107527 | 0.88172 |
| ME-584920 | 0.395062 | 0.604938 | 0.979592 | 0.020408 |
| ME-477191 | 0.394558 | 0.605442 | 0.280899 | 0.707865 |
| ME-573819 | 0.433121 | 0.566879 | 0.05618 | 0.921348 |
| ME-483910 | 0.489362 | 0.510638 | 0.875 | 0.111111 |
| ME-938210 | 0.382716 | 0.617284 | 0.34 | 0.64 |
| ME-492382 | 0.55625 | 0.44375 | 0.549296 | 0.422535 |
| ME-382810 | 0.474684 | 0.525316 | 0.493976 | 0.493976 |
| Average Panel Propensity | 0.433112 | 0.566888 | 0.483011 | 0.504647 |

In some embodiments, the medical panel module 222 may further be operable to facilitate communication of data or information to the medical experts comprising a panel. For example, the medical panel module 222 may be operable to retrieve, populate and/or transmit data into a user interface that is made accessible to the medical experts. In some embodiments, medical panel module 222 may be operable to facilitate making Opinion Request data available to medical experts via a web browser or mobile app. In one embodiment, the data necessary for a medical expert to provide an opinion for an Opinion Request may be output to the medical expert via one or more web pages rendered on a medical expert device 130 (e.g., the medical expert may be notified that his input to an Opinion Request is requested, via an e-mail or text, and may access the data by logging into his/her account of the services facilitated by Medical Panel Server 110 using a Medical Expert Device 130). In other embodiments, notifications and/or data may be communicated to a medical expert who has been selected to a panel using social media (e.g., post messages including the avatar or another representation of the user to sites such as FACEBOOK™, TWITTER™, TUMBLR™ or GOOGLE+™).

Referring now to FIG. 3A, illustrated therein is an example user interface 300A which embodies how data or information regarding an Opinion Request may be conveyed to a medical expert serving on a panel assigned to the Opinion Request. As illustrated in the figure, a Narrative field may be populated based on text, information or input provided by a treating physician when the treating physician submits an Opinion Request. The Accompanying Files field may, in accordance with some embodiments, store links to files (or, in some embodiments, other information or the files themselves) that may be helpful to the medical expert in providing the medical opinion. In the example embodiment of FIG. 3A, the Accompanying Files are X-Ray and MR images of relevant portions of the subject patient's spine. The medical expert may thus click on one or more of these files to view the images. In some embodiments, a treating physician (or an agent thereof, such as a nurse or administrative assistant) may upload medical files or records for a patient or authorize a $3^{rd}$ party service to provide such medical files or records to the medical panel service described herein. In some embodiments, no unique patient identifiers may be uploaded into the system to protect patient privacy to be HIPAA compliant. In some embodiments, these medical files or records may thus be made available to the medical expert for the subject patient of an Opinion Request via an interface such as that represented in FIG. 3A. In some embodiments, the medical files or records may be altered to protect the privacy of the subject patient (e.g., identifying information may be redacted and replaced with a patient identifier that, while uniquely identifying the patient, does not reveal the patient's identity to the medical expert). In some embodiments, such alteration or redaction of medical records or files may be one by the treating physician or a $3^{rd}$ party service that facilitates the transfer of such files or records to the medical panel service described herein while in other embodiments the medical panel service may perform such functions (e.g., via Medical Panel Server 110). In some embodiments, the system (e.g., system 200) may be operable to analyze or review images or records provided with an Opinion Request and, if the images or records are not sufficiently clear (e.g., the resolution is insufficient, the images are blurry or data in the images is otherwise obscured or unclear), the images or records may be flagged. In some embodiments, clearer images may be requested prior to a medical panel being assigned to the Opinion Request.

Figure 3B:
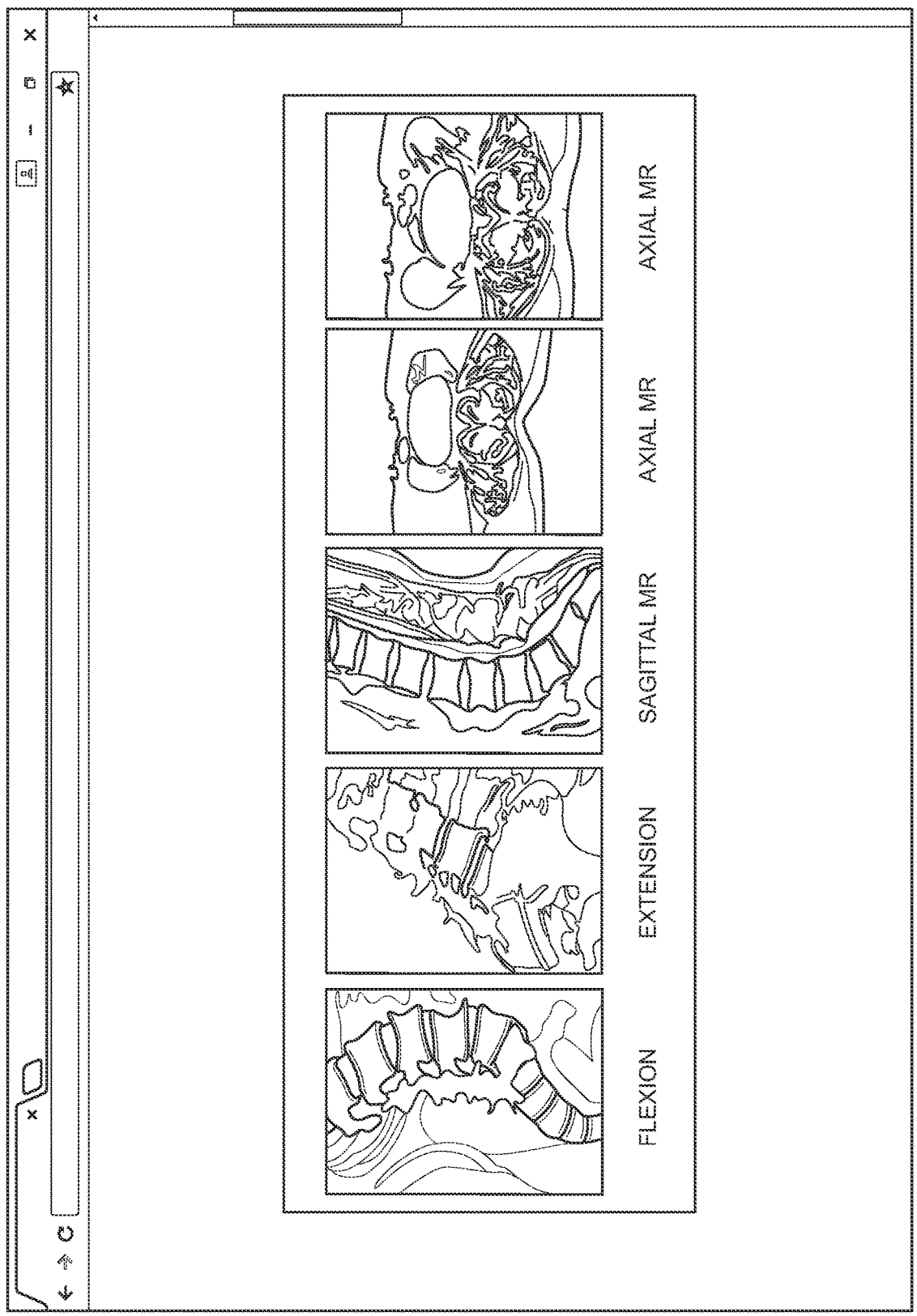

FIG. 3B illustrates, in accordance with one embodiment, a user interface 300B that may be output to the medical expert once the medical expert clicks on one or more of the files in the Accompanying Files field of interface 300A (FIG. 3A). Of course, other information, data or options may be output to a medical expert in order to facilitate the medical expert's provision of a medical opinion for an Opinion Request and the user interfaces of FIGS. 3A and 3B are examples only. For example, in some embodiments a field or feature of a user interface output to a medical expert may allow the medical expert to request additional information (e.g., from the system, from the treating physician or from a $3^{rd}$ party such as an entity that stores medical records for the patient, either directly or indirectly).

The Opinion Report module 224 may, in accordance with some embodiments, be operable to generate an Opinion Report for an Opinion Request as data comes back from medical experts comprising a panel. For example, the Opinion Report module 224 may be operable to receive input, selections or responses from medical experts serving on a given panel and analyze, summarize and track these for at least the purpose of producing an Opinion Report that is to be provided to the treating physician who submitted the corresponding Opinion Request. In one embodiment, the Opinion Report module 224 may be operable to perform analysis on the responses such as determining what percentage of experts voted for or recommended which option and to render this information in a summary, graph or other format for the treating physician. In accordance with some embodiments, the treating physician may in turn share the Opinion Report with the patient who is the subject of the Opinion Request.

In some embodiments, the methods or systems as described herein may include built-in checks or sub-routines to help ensure that medical experts are not merely selecting treatment options randomly or without thought. Thus, for example, some requests or information transmitted to medical experts may include faulty, incomplete or inconsistent data that should prompt the medical expert to request clarification, indicate an inability to provide an opinion or otherwise express an objection or concern with respect to the information if the medical expert is legitimately reviewing the information provided. For example, the system may randomly insert inconsistent data to some Opinion Requests and monitor the medical expert responses or feedback to determine whether the medical expert has caught the inconsistent data or provided an indication of awareness of the inconsistent data. If the medical expert does not indicate an awareness of the inconsistent data, a flag or alert may be generated by the system and the response(s) of that medical expert may be further reviewed by the system prior to being included in an Opinion Report.

Figure 3C:
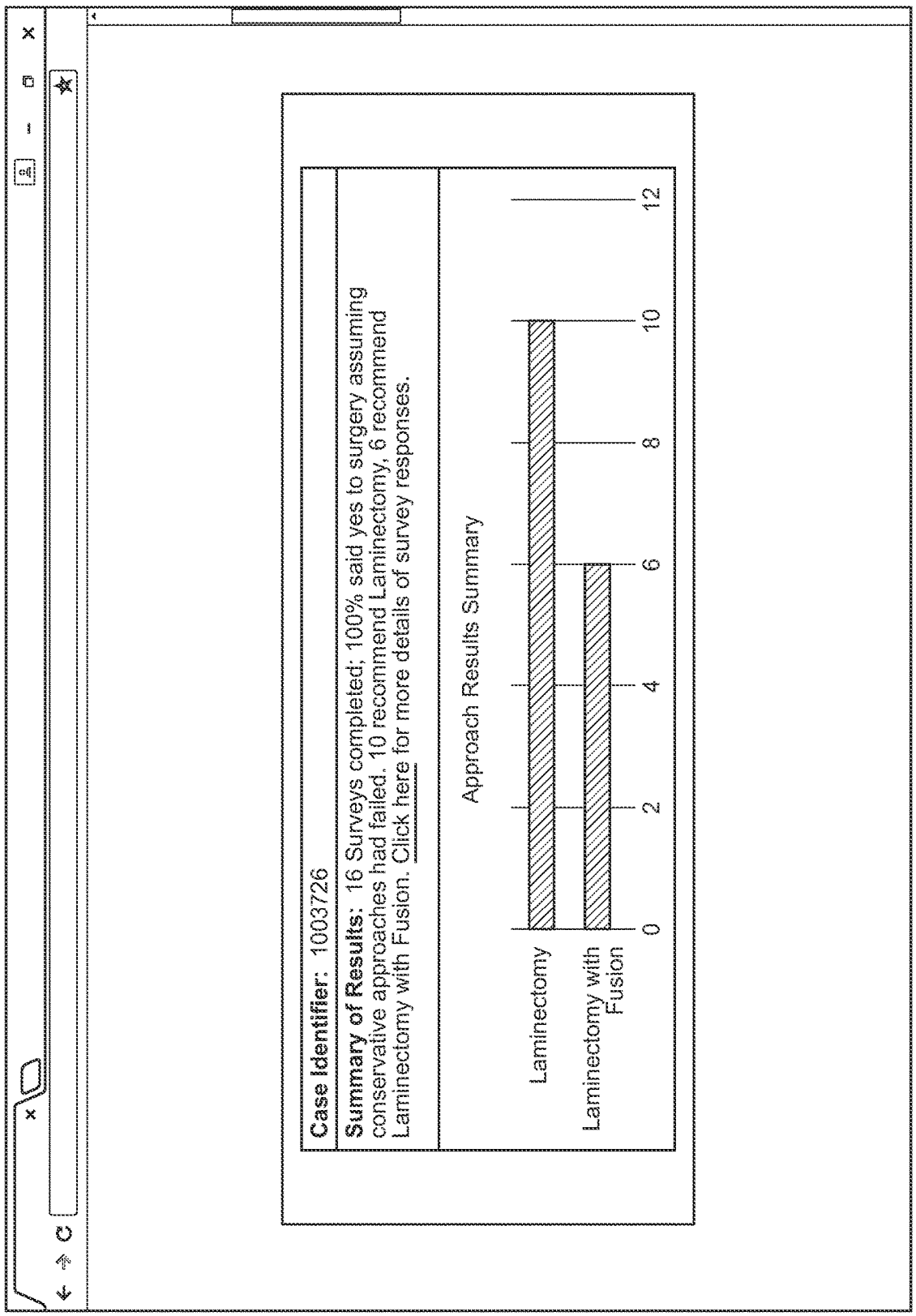

Referring now to FIG. 3C, illustrated therein is an example user interface 300C (illustrated as a web page rendered via a web browser output to a treating physician who has logged into his/her account of the medical panel service described herein). The user interface 300C illustrates one format of an Opinion Report that summarizes, in bar graph form, the results of opinions received from medical experts for a particular Opinion Request. For purposes of continuity, the Opinion Report illustrated in FIG. 3C is for the Opinion Request illustrated in FIGS. 3A and 3B (as evidenced by the Case Identifier 1003726, which may be a unique identifier assigned by the system and used to reference an Opinion Request to a corresponding an Opinion Report). In accordance with some embodiments, the user interface 300C illustrates that sixteen (16) medical experts have provided a medical opinion for the Opinion Request, that all of them agreed that surgery was the recommended treatment option assuming all other treatment options have failed and that while ten (10) of the medical experts recommend laminectomy alone, six (6) recommend laminectomy with fusion. While the Opinion Report is illustrated as an online report output on a web page, it is understood that other forms of such a report may be utilized and the embodiments described herein are not dependent on any particular form of outputting the information comprising an Opinion Report (e.g., a printed report or an e-mailed report may be provided).

In the "Summary of Results" section of the report, there is a link via which a treating physician may access more detailed information. FIGS. 3D-3E together illustrate a user interface that may be output to a user (e.g., a treating physician) who requests more detailed information about the opinions of the medical experts (whether by selecting the "Summary of Results" link or otherwise). In accordance with some embodiments, the detailed information about the opinions received from the medical experts includes a Medical Expert Identifier (a unique identifier that uniquely identifies the medical expert who provided the opinion), a recommended medical treatment approach selected by the corresponding medical expert and any corresponding comments that the medical expert may have provided.

It should be noted that the Medical Experts are not identified in the embodiment illustrated in FIGS. 3D-3E. While in some embodiments the identities of medical experts may be maintained as anonymous from a treating physician and/or the patient who is the subject of an Opinion Request, in other embodiments information about the medical expert may be made available (e.g., upon request). For example, one or more of the following may be made available to a treating physician and/or patient regarding a medical expert who served on a medical panel of an Opinion Report: (i) name; (ii) contact information; (iii) credentials; (iv) hospital or medical facility the medical expert is affiliated with; and (v) education or professional background and credentials. In some embodiments, the medical panel system may allow or facilitate a treating physician or patient contacting a medical expert directly regarding a medical opinion provided on an Opinion Report. For example, a patient may wish to make an appointment to visit a medical expert who provided an opinion or at least know more information about the medical experts who provided opinions for an Opinion Report. In another example, a treating physician may wish to contact a particular expert who provided a recommendation that is an outlier from other recommendations of the panel or who provided an interesting comment with his opinion/recommendation.

Although not illustrated in FIG. 2, it should be noted that additional and/or different modules, programs and/or data may be part of system 200. For example, in some embodiments medical experts may be compensated for participating in medical panels and a payment module may be part of system 200 in order to facilitate such payments (e.g., to the medical expert directly or to a medical practice, hospital or other medical institution with which the medical expert is affiliated). In another example, a treating physician or patient (or a medical practice, hospital or other medical institution, or an insurance provider of the patient) may provide a fee (e.g., per Opinion Request, on a subscription basis or otherwise) for Opinion Requests/Reports. In such embodiments, the system 200 may include a billing module to help facilitate the billing for its services.

The user interfaces of FIGS. 3A-3E may comprise, for example, user interfaces of a Medical Panel Service (such as may operate the Medical Panel Server 110 (FIG. 1), in one embodiment), for allowing a treating physician to request a plurality of second opinions from a plurality of medical experts with expertise in the relevant field, for a medical condition, diagnosis or recommended treatment for a patient for the treating physician and for allowing medical experts to provide such second opinions via a panel of experts that has been created by a system such as described herein. In one embodiment, a treating physician may register to use the services of the system in order to obtain Opinion Reports for one or more of his patients and thus reassure the patient that the recommended treatment that the treating physician is recommending to the patient is in line with what other medical experts in the relevant field are recommending for the patient. Medical experts may register with the system to provide second opinions via panels of experts in order to earn extra compensation for themselves, to earn grant money or other compensation for their research or a research institution or project of their choice, to burnish their credentials and/or provide reassurance and help to patients who may not otherwise be able to reach the medical experts directly.

Thus, in accordance with some embodiments, methods, systems and articles of manufacture may provide for a service that (i) receives an Opinion Request from a treating physician (including relevant patient data, records and/or files, whether from the treating physician, an agent thereof or a 3$^{rd}$ party service as authorized by the treating physician); (ii) selects a plurality of medical experts with expertise in the relevant medical field to serve on a panel providing medical opinions to the treating physician as to the recommended medical treatment and/or diagnosis for a patient who is the subject of the Opinion Request; (iii) provide to the medical experts comprising the panel the relevant patient information, records or files (based on information received from the treating physician), requesting that each medical expert provide an opinion responsive to the Opinion Request; (iv) receive responses from each of the medical experts comprising the panel; and (v) generate an Opinion Report for the Opinion Request based on the responses from the medical experts and transmit the Opinion Report to the treating physician.

Figure 4:
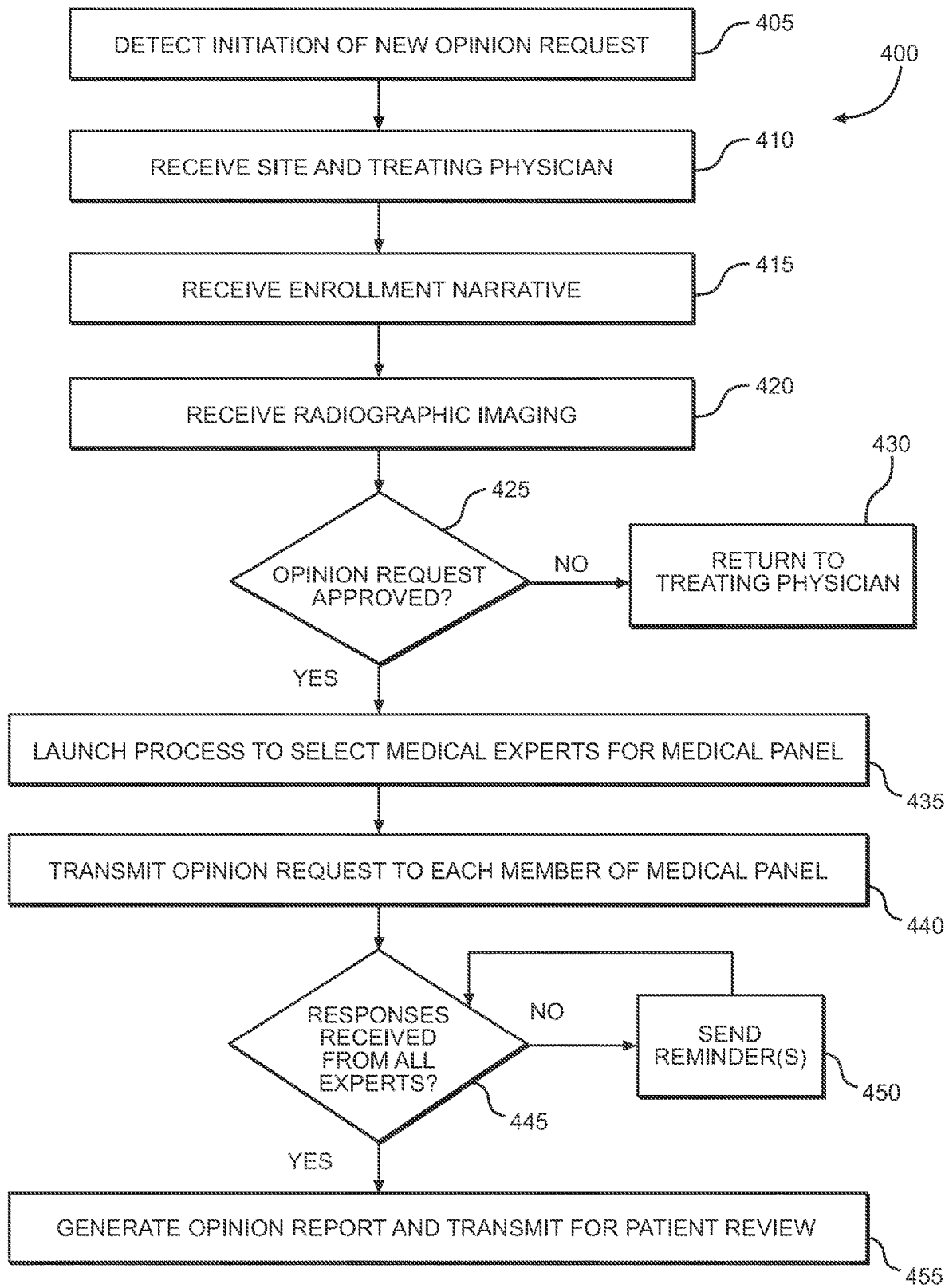
FIG. 4 comprises a flow diagram of an example process consistent with some embodiments described herein.

Referring now to FIG. 4, illustrated therein is a flow diagram of an example process 400 consistent with at least some embodiments described herein. It should be noted that the process 400 (and all processes described herein) are exemplary only and should not be construed in a limiting fashion. For example, additional and/or substitute steps to those illustrated may be practiced within the scope of the present invention(s) and in one or more embodiments one or more steps may be omitted or modified. In one embodiment, the process 400 (or portions thereof) may be performed, for example, by a Medical Panel Server 110 (FIG. 1) and/or system 200 (FIG. 2). The process 400 comprises an example method for obtaining a plurality of expert medical opinions for a patient in a timely, efficient and cost effective manner that retains and strengthens the relationship between a patient and his treating physician by performing at least one of the following functions: (i) selecting a panel of medical experts to provide "second opinion" treatment recommendations for a patient, based on data and information corresponding to the patient received from the patient's treating physician; (ii) tracking and updating a propensity score for each medical expert registered with the system to provide opinions as well as for each apprentice medical expert; (iii) performing attentiveness checks on the medical experts to whom Opinion Requests are sent; (iv) tracking responses and requests for additional information from medical experts to whom an Opinion Request has been sent; and (v) generating an Opinion Report for the patient based on the responses received on the corresponding panel of experts and, in some embodiments, transmitting the Opinion Report to the treating physician for sharing with the patient.

Referring now to FIG. 4 in particular, illustrated therein is a process 400. It should be noted that process 400 may be preceded by a registration process (not shown) in which a medical expert applies to or registers with the Medical Panel Service. During such an application or registration process, a medical expert who would like to receive Opinion Requests from the Service and provide treatment recommendations to patients through the Service may input some information about him/herself that allows the Service to verify the medical expert's qualifications and credentials (e.g., in some embodiments the Medical Panel Service may contact one or more third parties, such as the medical expert's place of employment, medical facility that the medical expert is affiliated with or the school(s) at which the medical expert studies, in order to verify credentials and/or seek reference information). In some embodiments, a medical expert who is newly accepted into the Service may initially be designated as an "apprentice" medical expert. An apprentice medical expert, in accordance with some embodiments, may be allowed to participate in the Medical Panel Service in a passive capacity (e.g., for a predetermined period of time, a predetermined number of Opinion Requests or until another predetermined criteria is satisfied) such that, while the apprentice medical expert may be included on Opinion Requests, the treatment recommendations provided by the medical expert while he/she is designated as an apprentice may be recorded for certain purposes (e.g., to build a propensity score for the medical expert) but not included in an Opinion Report generated for a patient. Other types of preliminary registration processes may also precede process 400. For example, participating medical sites (e.g., hospitals or other medical provider facilities), treating physicians and/or patients may register with the Medical Panel Service prior to being able to submit Opinion Requests to the system.

It should be noted that a reference to Medical Panel Service herein may, unless indicated otherwise, be applicable or interchangeable with a reference to a medical panel server 110 (FIG. 1) and/or system 200 (FIG. 2) as described herein, or services that correspond to methods or processes carried out with the aid of such medical panel server 110 and/or system 200. For example, when it is described that data or information is provided to the Medical Panel Service, it may be interpreted that the data or information is provided to the system 200 (e.g., directly via an input device of the system 200, over a network from a remote device of a user or third party organization or to personnel or an agent of the Medical Panel Service, who may proceed to enter the data or information to the system 200).

Figure 5A:
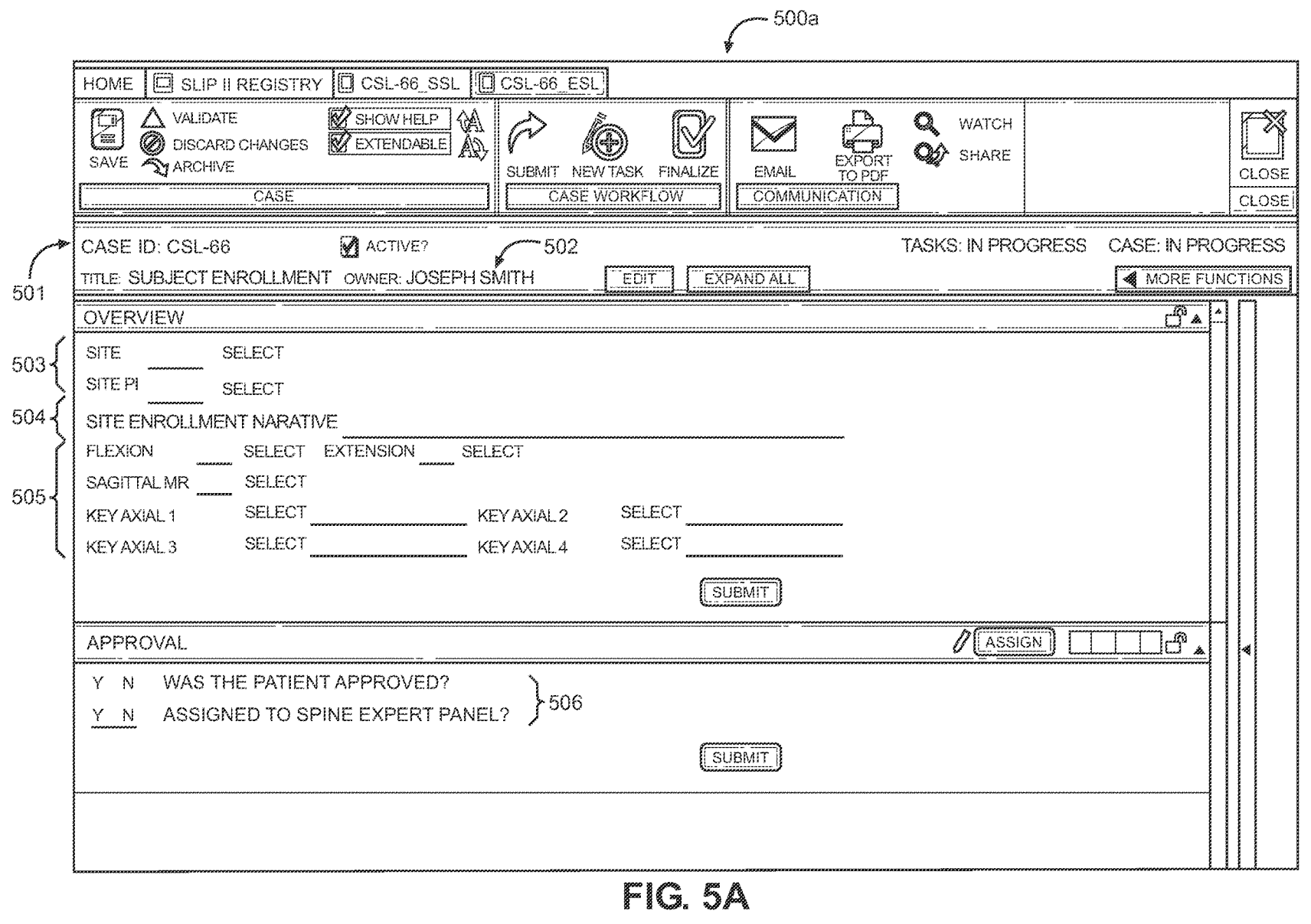
Figure 5B:
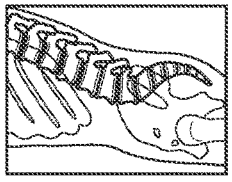

Process 400 of FIG. 4 will now be described with occasional reference to FIGS. 5A-5D, which illustrate some user interfaces that may be implemented in accordance with the embodiments described with respect to process 400. In step 402 of process 400, an initiation of an Opinion Request is detected. For example, medical panel server 110 may receive an indication that a user (e.g., a treating physician or an agent of a treating physician) has begun inputting data defining a new Opinion Request (e.g., a request for a plurality of "second" opinions regarding the recommended treatment option for a patient of the treating physician. While in some embodiments such Opinion Requests may be initiated by or on behalf of a treating physician (e.g., with permission from the patient who is the subject of the Opinion Request), in other embodiments it may be the patient who initiates the Opinion Request. Detecting an initiation of a new Opinion Request may comprise, for example, detecting that a user who has previously registered with the system has logged in and selected an option to initiate a new Opinion Request or has begun entering data into a user interface for submitting a new Opinion Request. In some embodiments, a unique patient or case identifier may be generated and assigned to the Opinion Request by the system. The user interface 500A of FIG. 5A is an example of a user interface that may be utilized to submit information for a new Opinion Request. In the example embodiment of FIG. 5A (and FIGS. 5B and 5C, each of which illustrate different aspects, tabs or fields of the user interface initially illustrated in FIG. 5A), the submission of a new Opinion Request is referred to as a "subject enrollment", the subject being the patient. Thus, enrolling a patient into the system may refer to submitting information about the patient in order to obtain an Opinion Report for the patient and thus obtain a plurality of expert medical opinions as to recommended treatment options for the patient's medical condition.

In accordance with some embodiments, the name and/or other identifying information about a patient may be entered into the system when enrolling the patient into the system. Example user interface 500A (FIG. 5A), in accordance with one embodiment, illustrates in field 502 that the name of the patient being enrolled in the illustrated example is "Joseph Smith." Such patient identifying information may, however, be withheld from the medical experts included on the medical panel generated for the patient's Opinion Request.

In some embodiments, a unique identifier may be assigned to an Opinion Request and/or a patient in order to uniquely track that patient and Opinion Request responses within the system. Example user interface 500A (FIG. 5A), in accordance with one embodiment, illustrates in field 501 that a unique "Case ID" of "CSL-66" has been assigned to patient Joseph Smith. In accordance with some embodiments, the version of an Opinion Request that is eventually going to be sent to the medical experts on a panel generated by the system for the subject patient will include only an identifier that, while uniquely identifying the patient and/or Opinion Request, maintains the anonymity of the patient with respect to the medical experts who are reviewing the patient's information (e.g., such as the Case ID illustrated in field 501 of user interface 500A).

In accordance with some embodiments, specific types of information may be received in an Opinion Request submission or during the enrollment process for a patient, information that is geared towards helping a medical expert provide an informed recommendation for a treatment plan or treatment options for the patient and information that allows the system to conduct follow-up communications with the submitting treating physician (e.g., provide an Opinion Report, request additional information or clarifications to submitted data, obtain payment of a fee, etc.). The information should provide personalized and relevant context for the patient's medical condition and the relevant radiographic images or other medical files that a medical expert in the relevant medical field would reasonably want to have before providing a treatment recommendation specific to the patient. In one embodiment, as illustrated in process 400, the treatment site and treating physician of the subject patient may be received (step 404), as well as an enrollment narrative (step 406) and radiographic imaging or other medical files (step 408).

The enrollment narrative may comprise, for example, a brief summary of symptoms or other signs of the relevant medical condition, duration and location of symptoms, previous treatment attempts and results, what eases and/or increases pain, relevant patient-reported quality of life issues, age, gender and other information that a medical expert in the relevant field may find reasonably relevant to deciding on a recommended treatment option. The user interface 500A illustrates an area 503 which allows for input of a site and a treating physician (e.g., via respective drop down menus that show a menu of registered sites and physicians) as well as an area 505 that allows for an input of an enrollment narrative. In some embodiments, the enrollment narrative may include an audio and/or video file (e.g., of the patient and/or treating physician providing information about the patient, patient's medical history and/or quality of life, medical condition, etc.).

In accordance with some embodiments, one or more radiographic images or other medical files may be uploaded to the system as part of an Opinion Request. In the example of FIGS. 5A-5D, the medical condition for which treatment recommendations are being sought from a panel of medical experts is a spine condition. Thus, the relevant radiographic images that are suggested or requested to be uploaded include a Flexion radiographs, Extension radiographs and axial images of vertebrae (e.g., to show whether there is a possible disease such as nerve impingement and/or narrowing of a spinal column). User interface 500A illustrates, in area 505, selections which a user may select to indicate which types of radiographs or images the user desires to upload for the Opinion Request being submitted. It should be noted that, in accordance with some embodiments, the system may be operable to interface or communicate with a third party service that facilitates the transfer or uploading of such medical radiographs, images or other files. In such embodiments, the user's selection of one of the options in area 505 may trigger, for example, a process or subroutine for the medical panel server 110 to communicate with such a third party service in order to obtain the indicated files. In some embodiments, the user (e.g., agent of the treating physician who is requesting the Opinion Request) may need to provide credentials or an identifier for the patient and/or the particular files, which the medical panel server 110 may utilize in order to request the files from the third party server. In other embodiments, the user may upload the files to the system, either directly (e.g., from their device, such as physician device 120 (FIG. 1)) or indirectly by facilitating the transfer of the files from the third party service.

Figure 5C:
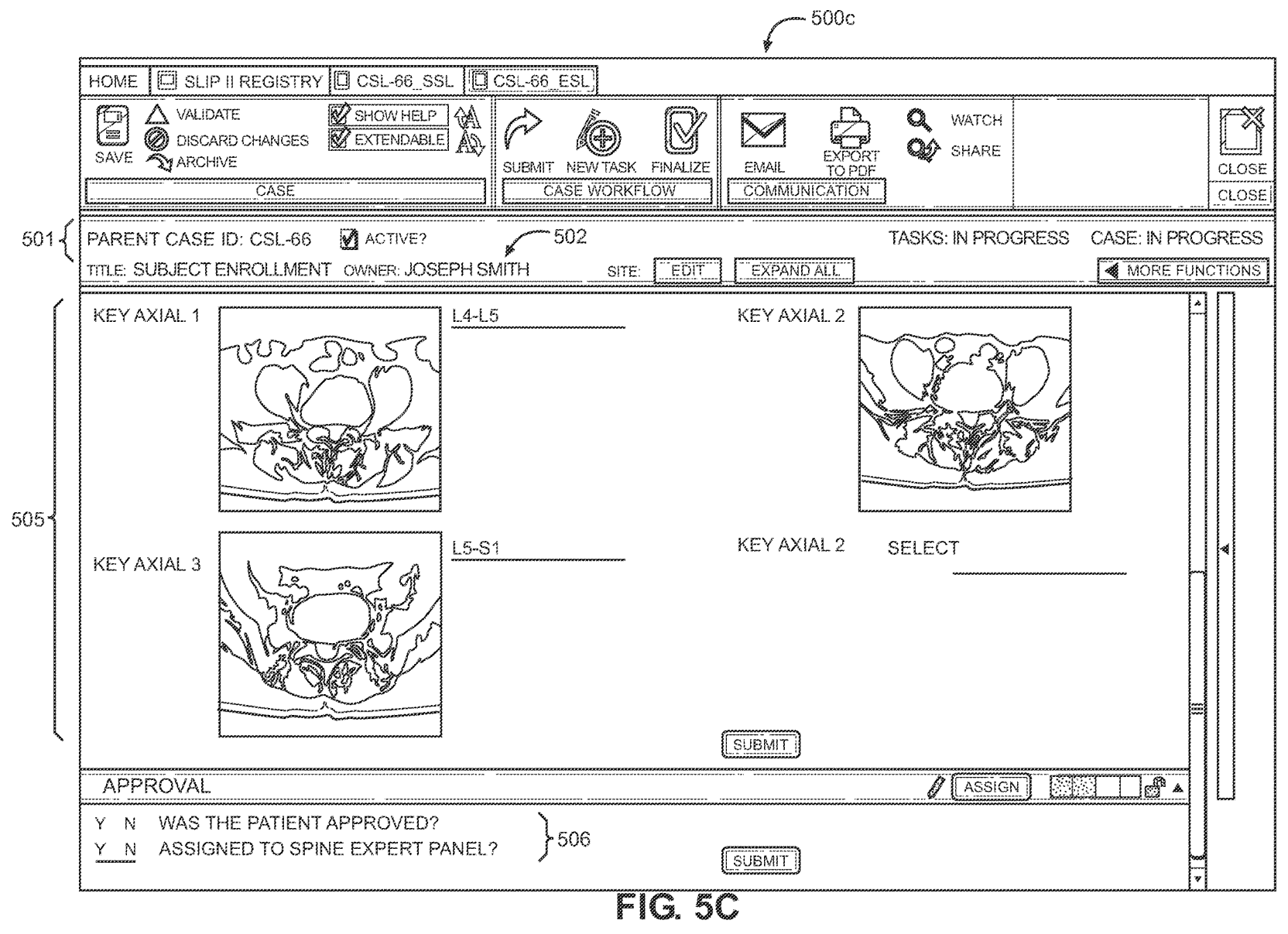

Turning briefly to FIGS. 5B and 5C, the user interfaces illustrated therein illustrate how the user interface 500A may appear once the user has an enrollment narrative and several radiographic images for an Opinion Request. In particular, user interface 500B (FIG. 5B) illustrates an enrollment narrative as having been entered into area 504 for patient "Joseph Smith" as well as a representation of a "flexion" radiograph, an "extension" radiograph" and a "sagittal MR" radiograph in area 505, indicating that these files have been uploaded to the record for this patient's Opinion Request. User interface 500C (FIG. 5C) illustrates in area 505 several additional radiographs as having been uploaded for patient "Joseph Smith": 3 key axial radiographs.

In some embodiments, the type of information that is required or recommended to be provided may be dependent on the type of medical condition or diagnosis for which an Opinion Request is being submitted. For example, in some embodiments medical experts in different areas of expertise (e.g., spinal disease, prostate cancer, brain cancer, knee injuries or conditions) may be available for the formation of medical panels and thus a user submitting information for an Opinion Request may need to provide an indication of the type of medical condition that the Opinion Request is related to. For example, a user interface for inputting information defining an Opinion Request (such as user interface 500) may include a drop-down menu or other mechanism via which the user may indicate the general field or medical condition pertaining to the patient. In some embodiments, the selection of this general area or medical condition may drive different aspects of how the Opinion Request is processed. For example, the selection or indication by the user of the medical condition may determine what fields are shown to the user in the user interface. For example, the types of medical records are recommended or required for upload (e.g., in area 505 of user interface 500A) may be modified based on the type of medical condition (e.g., a biopsy result may be required for some medical conditions but not others, a radiograph or certain type of radiograph may be required for other medical conditions). The type of medical condition may also cause additional fields or information to be requested and may be used to select the particular medical experts to be included on a medical panel generated for the Opinion Request. Thus, in accordance with some embodiments, process 400 or another process may include receiving from a user inputting an Opinion Request an indication of the medical condition (or general area of medical expertise) relevant to the Opinion Request and this indication may be utilized to select or modify other aspects of the process or other processes.

Turning again to FIG. 4 and process 400, once the enrollment narrative, relevant radiographs or other medical files and any other information required in order for the Opinion Request to be processed further by the system are received, the process continues to step 425, in which the Opinion Request is submitted for approval. In accordance with some embodiments, before a panel of medical experts is selected for an Opinion Request, the information/data submitted by a user (e.g., treating physician, agent of treating physician or patient) defining the Opinion Request is reviewed for approval for forwarding to a panel of medical experts. The approval process may be performed by personnel of the Medical Panel Service, may be an automated process, or a combination thereof. The approval process may comprise, for example, verifying that there is sufficient information/data provided in order for a medical expert to be able to provide a reasonably informed treatment recommendation. In some embodiments, the approval process may comprise reviewing the radiographs or other medical files to verify that they are sufficiently clear (e.g., in terms of resolution), that the size of the files does not exceed certain parameters and that the enrollment narrative provides reasonably relevant and sufficient information. In some embodiments, an agent of the Medical Panel Service may be assigned to review the Opinion Request and either approve it or request additional data from the user who submitted the Opinion Request. If an approval of the Opinion Request is received, the process 400 continues to step 435. If not, the process continues to step 430, in which step the user who submitted the Opinion Request (e.g., the treating physician or agent of the treating physician) is contacted to submit the additional clarifications, data or information that was determined to be necessary in order for the Opinion Request to be approved for forwarding to the panel of medical experts.

It should be noted that, in accordance with some embodiments, at least some of the steps 410-430 may be performed by a medical data assembly module, which may comprise a set of instructions or program of the medical panel server 110 operable to receive and process data for an incoming Opinion Request (e.g., data assembly module 220 of system 200 (FIG. 2)).

In step 435, the process of selecting a panel of medical experts to whom the Opinion Request is to be forwarded is initiated. In some embodiments, this process may be a separate subroutine or process while in other embodiments this process may be part of process 400. In some embodiments, the subroutine or process comprising step 435 may be performed by medical panel module 222 of system 200 (FIG. 2). In accordance with some embodiments, the selection of medical experts for a panel of medical experts to which a specific Opinion Request is to be sent may be based on at least one of the following criteria: (i) a propensity score for available medical experts; (ii) a desired range or average propensity score for the panel; (iii) an availability of medical experts; (iv) an area of medical expertise of the available medical experts as compared to the relevant medical condition; (v) a desired geographic diversity of the panel (e.g., as requested by the patient or treating physician or as set by the system); (vi) a history of activity with respect to being selected for panels for available medical experts (e.g., the system may be programmed to not exceed a predetermined frequency, or attempt not to except, a certain number of Opinion Requests sent to a given medical expert within a given time frame (e.g., attempt not to exceed one Opinion Request per week for a given medical expert); (vii) fees associated with available medical experts or a desired maximum cost of the resulting panel (e.g., in embodiments in which experts are paid to serve on a panel and different experts are paid different amounts, the total amount to be paid for a given panel may be set to not exceed a predetermined amount); and (viii) one or more preferences associated with available medical experts.

As described with respect to FIG. 2, in accordance with some embodiments the medical panel module 222 may be operable to create and facilitate the putting together of medical panels for received Opinion Requests using at least some data stored in memory 202 by utilizing one or more rules or algorithms when selecting the particular medical experts to include in a panel. Such rules or algorithms may take into account various factors, such as how many panels an expert has been placed on within a particular time frame, in order to load balance the number of Opinion Requests that are forwarded to a given medical expert within a particular time frame, the expertise or credentials of available experts and/or feedback or reviews from patients and/or treating physicians.

As described herein, in some embodiments, a propensity score may be generated for each potential or available medical expert and medical experts may be selected for a medical panel based on such propensity scores (e.g., to achieve a propensity score within a desired range for a given panel, when the propensity scores of the medical experts on that panel are averaged, summed or otherwise combined). A propensity score may, in some embodiments, comprise a quantitative indication of how likely a medical expert is to recommend one treatment option over another (for a given medical condition or type of medical condition). In accordance with some embodiments, a propensity score for a given medical expert registered with the system may be generated and updated over time as the medical expert responds to Opinion Requests by recommending treatment options. For example, in one embodiment, a subroutine or process performed by the Medical Panel Service calculates and re-calculates the propensity score for a given medical expert each time the medical expert serves on a medical panel and provides a response to an Opinion Request. Thus, the propensity score for the medical expert may be an up-to-date reflection of what treatment option the medical expert recommended in the past (e.g., for a given medical condition) and may be used by the system as a predictive mechanism for predicting how likely the medical expert is to recommend one treatment option over another in the next Opinion Request (s)he is provided. In accordance with some embodiments, the Medical Panel Service may strive to avoid generating a panel of experts who are, as a group, more likely to recommend a first treatment option over another treatment option and thus be considered as biased towards the first treatment option for a given medical condition irrespective of the specific patient data/circumstances. In some embodiments, the system (e.g., via the medical panel module operable to select the medical experts for a given panel) may strive to avoid such a seemingly biased panel by selecting medical experts for a given panel based at least in part on their propensity scores. For example, the medical panel module may be programmed to select medical experts such that the average propensity score for the selected medical experts is within a certain desired rang.

In accordance with some embodiments, a propensity score may be anywhere between "0" and "1" the desired average propensity score for a given panel may, in some embodiments, be between 0.4 and 0.6. In other embodiments, the desired average propensity score for a panel may simply have an upper limit (e.g., 0.8). In some embodiments, rather than selecting medical experts for a panel such that the average propensity score of the selected experts is within a desired range or limit, medical experts may be excluded from a panel if their propensity score is outside of a desired range or above an upper limit. For example, in one embodiment any medical expert with a propensity score above 0.8 for a given medical condition and treatment option may be excluded.

As described herein, in some embodiments, a medical expert who is newly registered with the system may be designated with a special status of "apprentice" and thus be associated with certain limitations in terms of his/her participation in the system. For example, an apprentice medical expert, while able to receive Opinion Requests and being asked to provide a recommended treatment option for the received Opinion Requests, may have his/her opinion or treatment recommendation be utilized for limited purposes by the system, such as to calculate or update a propensity score for the medical expert, but not have it included on a resultant Opinion Report for the Opinion Request. In some embodiments, there may be other special designations associated with medical experts registered with the system that similarly limit their participation in the system. For example, in some embodiments if the propensity score for a medical expert rises above an upper desired limit (e.g., 0.8), that medical expert's status within the system may be modified to a "probation" or "limited" status such that, while the medical expert may receive Opinion Requests and be asked to provide an opinion/recommended treatment option, the response from the medical expert may be utilized only to update his propensity score and not included on a resultant Opinion Report for the corresponding Opinion Request. In such embodiments, once the medical expert's propensity score is again within an acceptable range or at/below an upper limit, the medical expert may be returned to a regular status and his/her responses may once again be included on Opinion Reports. In accordance with some embodiments, medical experts who have a special status such as "apprentice", "probation" or "limited" may be treated differently by the system in other respects. For example, a medical expert with certain special status may not be compensated for providing responses to Opinion Requests (in embodiments in which medical experts are so compensated) or may be compensated at a reduced rate/scheme.

In accordance with some embodiments, step 435 may comprise not only selecting the particular medical experts to include on a panel but also selecting one or more medical experts who have a special status (e.g., apprentice, probation or limited) and to whom the Opinion Request is to be sent but whose responses are not to be included on a resultant Opinion Report. Such special status medical experts may be selected, for example, based on their qualifications and a determination of which such medical experts need additional data for updating their propensity scores.

In some embodiments, medical experts may set certain preferences or parameters for use by the system in determining whether to place a given medical expert on a medical panel (e.g., a maximum number of Opinion Requests the medical expert is willing to respond to in a given time period). Such preferences or parameters may be stored, for example, in medical expert data records 208 and the medical panel module 222 may utilize such preferences or parameters when creating a panel.

In some embodiments, the Medical Panel Service may commit to providing an Opinion Report within a maximum period of time from having received a submission of an Opinion Request (e.g., within seventy-two (72) hours, two (2) weeks or one (1) month). In many cases a patient who has received a serious medical diagnosis is anxious to decide on and begin a recommended treatment plan in a timely manner and providing an Opinion Report relatively quickly may be an important aspect of the Service. Accordingly, in some embodiments the selection of medical experts for a panel may be at least partially based on (i) an availability of a given medical expert to provide a response to an Opinion Request within a required timeframe; and/or (ii) a measure of how long it has taken the medical expert to provide responses to Opinion Requests in the past.

In accordance with some embodiments, medical panels are composed of individuals with recognized expertise in the field relevant to a given Opinion Request. For example, a medical expert being considered for a medical panel responsive to a particular Opinion Request may have published multiple peer-reviewed articles demonstrating their globally recognized expertise in a field relevant to the medical condition of the patient who is the subject of the Opinion Request for which a medical panel is being formed.

In accordance with some embodiments, geographical locations of medical experts may be one of the criteria on which selection of medical experts for a panel is based. For example, in one embodiment it may be desirable to include at least one medical expert from a certain geographic region (e.g., Europe or South America), to include at least one medical expert from a country other than the patient's country, to include at least one medical expert within a day's driving distance to the patient's home town (e.g., so the patient can have a reasonable opportunity to follow up in person with at least one of the medical experts on the panel). Thus, in some embodiments, geographical diversity, proximity or other geographical considerations may be relevant to the selection of medical experts on a panel.

In accordance with some embodiments, medical panels may comprise groups of 10-15 medical experts. The particular number of medical experts on a given panel may vary depending on various factors, such as the clinical problem or medical condition involved, the number of medical experts available to serve on a given panel and/or the number of medical experts requested in an Opinion Request (in embodiments in which a treating physician is provided a choice in such number). In some embodiments a treating physician (or other entity, such as the medical institution with which a treating physician is affiliated, a patient or a patient's insurance provider) may provide a payment to the system for Opinion Requests/Reports (e.g., per Request/Report or on a subscription basis that may have a maximum number of such Requests/Reports per month or other timeframe). In such embodiments, there may be different tiers or categories of Opinion Requests/Reports available from the system, with the number of medical experts on a given panel dependent on the category of Opinion Request/Report involved.

Once the medical experts for a panel are selected, Opinion Requests may be transmitted to the selected medical experts (Step 440). As described herein, transmitting an Opinion Request to a medical expert of a panel may comprise retrieving, populating and/or transmitting data into a user interface that is made accessible to the medical expert and/or making Opinion Request data available to medical experts via a web browser or mobile app. In one embodiment, the data necessary for a medical expert to provide an opinion or recommended treatment option for an Opinion Request may be output to the medical expert via one or more web pages rendered on a medical expert device 130. For example, the medical expert may be notified that his input to an Opinion Request is requested, via an e-mail or text, and may access the data by logging into his/her account of the services facilitated by Medical Panel Server 110 using a Medical Expert Device 130. In other embodiments, notifications and/or data may be communicated to a medical expert who has been selected to a panel using social media (e.g., post messages including the avatar or another representation of the user to sites such as FACEBOOK™, TWITTER™, TUMBLR™ or GOOGLE+™).

As an example of information that may be output to a medical expert for the Opinion Request illustrated in FIGS. 5A-5C, the medical expert may be provided with the enrollment narrative of area 504 of user interface 500B and the radiographs (or links to the radiographs) indicated in area 505 of user interface 500B and/or user interface 500C. The medical expert may then be asked to respond to a simple poll or questionnaire. For example, the medical expert may be asked to select a treatment option from a plurality of reasonable treatment options for the patient's medical condition. For example, reasonable treatment options for the patient data illustrated in FIGS. 5A-5C may include (i) no surgery instrumented interbody fusion; (ii) instrumented fusion; (iii) non-instrumented fusion; (iv) open decompression; and (v) MIS decompression). In some embodiments, the medical expert may be asked to answer a few simple questions in the poll or Opinion Request (e.g., "Do you recommend surgery?", "Do you recommend fusion?"). The medical expert may also be encouraged to provide a free-form response or comments into a field provided for this purpose (e.g., "provide your suggested response") and/or comments on any assumptions or specific information about the patient that the medical expert is basing his recommended treatment option on. FIGS. 3A and 3B illustrates example user interfaces that embody how data or information defining an Opinion Request may be conveyed to a medical expert serving on a panel assigned to the Opinion Request and has been described in detail above and will not be repeated herein for purposes of brevity.

In accordance with some embodiments, each medical expert on a given panel may only be able to view their own response and not the responses of the other medical experts on the panel, at least until the Opinion Report is generated and provided for the patient. In some embodiments, the medical experts on a panel may be able to view each other's responses and/or the resulting Opinion Report once all responses are received. In other embodiments, medical experts on a panel may be able to view each other's responses even before all responses are in or before an Opinion Report is generated.

As described herein, in some embodiments a benefit of the Medical Panel Service is to obtain a plurality of second opinions for a patient within a relatively short amount of time (e.g., 72 hours or 1 week), such that the patient may be provided with the plurality of second opinions in a much shorter amount of time than the patient could reasonably have obtained them via conventional means (e.g., by visiting the plurality of individual medical experts, providing his/her medical files or subjecting him/herself to additional tests, scheduling and driving to the appointments, etc.). Thus, in some embodiments a medical expert may have a maximum amount of time within which he/she needs to provide a response to an Opinion Request. In some embodiments step 445 may comprise determining whether responses have been received from the medical experts to whom the Opinion Request was sent. This determination may be made by some predetermined period of time before the Opinion Report is due to be generated and provided for the patient (whether directly to the patient or to the patient's treating physician, for dissemination to the patient). For example, if the Opinion Report is due to be provided within four (4) days of the Opinion Request having been submitted, step 445 may be performed two (2) days before the Opinion Request is due to be generated. If not all of the responses that are expected have been received, process 400 may continue to step 450, in which step reminders may be sent (e.g., via e-mail and/or text messages) to the medical experts who have not yet submitted a response). If it is determined that all expected responses have been received, process 400 continues to step 455.

In accordance with some embodiments, steps 440-450 may be performed by or with the aid of the medical panel module 222 (system 200, FIG. 2) or another module such as a polling module that is configured to transmit Opinion Requests to medical experts of a panel (which may also be referred to as a polling of the medical experts on the panel), receive responses, determine whether reminders need to be sent to the medical experts from whom responses have not yet been received and/or whether any follow-up communications are needed based on any of the responses (e.g., a medical expert may request additional information about a patient, in which case the polling module may cause the request for additional information to be transmitted to the treating physician, agent of the treating physician, patient or other use who submitted the Opinion Request).

Figure 5D:
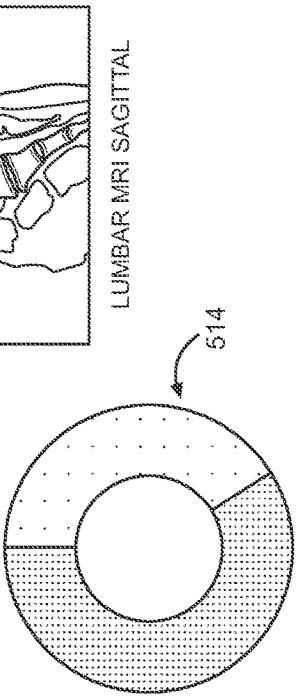
FIG. 5D comprises a rendering of an example Opinion Report that may be generated for a patient in accordance with at least some embodiments described herein.

Once it is determined that all expected responses have been received, an Opinion Report is generated for the patient who was the subject of the corresponding Opinion Request (step 455). The Opinion Report may be generated by or with the aid of, for example, a Opinion Report module or subroutine (e.g., opinion report module 224 of system 200 (FIG. 2)). In accordance with some embodiments, the Opinion Report may provide a summary of the responses to the Opinion Request as received from each of the medical experts on the panel (e.g., count of how many of the medical experts on a given panel recommended each available treatment option) in one or more forms (e.g., a bar graph as well as a pie chart). In some embodiments, the Opinion Report may also indicate identifying and/or contact information for each of the medical experts included on the panel, as well as any comments provided by any of the medical experts. FIG. 3C illustrate one example of how information or data comprising an Opinion Report may be conveyed to a treating physician and/or patient and, in accordance with some embodiments, is illustrated as a web page rendered via a web browser. The data illustrated in FIG. 3C is based on the data illustrated in the Opinion Request data illustrated in FIGS. 3A and 3B. FIG. 5D illustrates another format an Opinion Report may be embodied as (e.g., a report that can be printed out and provided to a patient by a treating physician). The data illustrated in FIG. 5D is based on the Opinion Request data illustrated in FIGS. 5A-5C.

In accordance with some embodiments, an Opinion Report may be generated "for" a patient but may not be provided directly "to" the patient by the Medical Panel Service. For example, in some circumstances it may be desirable to provide the Opinion Report to a patient while preserving the physician-patient relationship between the patient and his treating physician. Thus, in some embodiments an Opinion Report, while generated for a patient, may be provided to the treating physician of the patient, who may in turn disseminate or share the Opinion Report with the patient. This allows the information in the Opinion Report to ultimately be shared with the patient but within the context of the relationship between the patient and his treating physician. This may allow the treating physician to help explain the information in the Opinion Report to the patient, answer any questions the patient may have about the information in the Opinion Report and help build trust between the patient and his treating physician. Providing the Opinion Report to the patient through the treating physician may also avoid potentially creating a doctor-patient relationship (or implication of such) between the patient and a medical expert who provides an opinion or recommendation for the Opinion Report. In other embodiments, the Opinion Report may be provided directly to the patient who is the subject of the Opinion Report or through another entity (e.g., via an insurance provider of the patient).

In accordance with some embodiments, the Medical Panel Service may continue to obtain data regarding a patient after the Opinion Report is provided for the patient (whether such Opinion Report had been provided directly or through the patient's treating physician). For example, in some embodiments the Medical Panel Service may request that a patient for whom an Opinion Report was provided answer some questions or fill out data regarding his/her medical condition. The Medical Panel Service may send a request for such follow-up information to a patient directly or indirectly (e.g., via the patient's treating physician or insurance provider). The type of information that may be collected on a patient over time after an Opinion Report is provided for the patient may include, for example, (i) an indication of the patient's work status (e.g., was the patient able to return to work, to full time work, to all duties, etc.); (ii) the patient's quality of life; and (iii) the extent of the patient's return to full mobility or recovery from his/her medical condition. In accordance with some embodiments, if the obtained follow-up information from a patient indicates that the most recommended treatment option in an Opinion Report was not effective in improving the patient's medical condition, the patient's quality of life has not sufficiently improved or the outcome for the patient has been otherwise unsatisfactory, the system may take some action with respect to the patient. For example, a portion of a fee that had been paid to the Medical Panel Service for the Opinion Report (e.g., by at least one of the patient, the treating physician, the site with which the treating physician is affiliated and the patient's insurance provider) may be refunded.

FIG. 6A illustrates one example interface that may be utilized to obtain (e.g., during the patient's visit with their treating physician) information about a patient at (i) three (3) months after an Opinion Report; and (ii) six (6) months after an Opinion Report. FIG. 6B illustrates another example interface that may be utilized to obtain information about a patient (e.g., during the patient's visit to their treating physician at one (1) year after an Opinion Report), including additional medical files such as radiographs that may be uploaded at the time to illustrate the extent of the patient's recovery. In some embodiments the follow-up information on a patient's recover may be utilized by the Medical Panel Service to evaluate the effectiveness of the panel's recommendations. In some embodiments the follow-up information on a patient's recover may be made available to the medical experts who had been on the panel for the patient's Opinion Report.

As described above, in some embodiments the system may be operable to test a medical expert's attentiveness when responding to an Opinion Request (e.g., to verify the credibility and value of its Opinion Reports, by putting in place processes to guard against medical experts who may simply select a recommended treatment option without reviewing the information provided to them in an Opinion Request). For example, the system may be operable to test an attentiveness of a medical expert by transmitting to the medical expert a faux Opinion Request that is disguised as an authentic Opinion Request but which includes at least one element of information that is incompatible with a remainder of the information included in the request (e.g., a radiograph of a body part that is not relevant to the medical condition of the patient, a nonsensical enrollment narrative, a corrupt file that cannot be opened, medical facts that are not relevant or not compatible with the diagnosed medical condition of the patient, etc.). The system may be operable to send such faux Opinion Requests randomly or once very predetermined period of time or number of Requests sent to the medical expert (preferably in an unpredictable manner such that the medical expert cannot anticipate which Opinion Request may be a faux one). In such embodiments, the system may flag the faux request and await a response from the medical expert that indicates the medical expert caught the faux or incompatible information and is seeking clarification or otherwise noting his/her inability to provide a treatment recommendation based on the information provided. In some embodiments, if the medical expert does not provide a response that evidences his/her attentiveness (e.g., the medical expert provides a recommended treatment selection as if the Opinion Request were a genuine one), the system may take additional action. For example, an alert may be sent to personnel of the Medical Panel Service, noting the medical expert's failure to identify the Opinion Request as a faux one. In another example, an investigation protocol may be initiated (e.g., other responses to other Opinion Requests provided in the past by the medical expert may be reviewed and/or an additional faux Opinion Request may be transmitted to the medical expert to again test his attentiveness and/or system personnel may become alerted to look into the medical expert's responses). In yet another example, the status of the medical expert may be changes to a special status that, at least temporarily, limits the medical expert's participation in the system (e.g., the medical expert may be identified as "on probation"). In some embodiments, a fee otherwise payable to the medical expert may be downgraded (e.g., the medical expert may be paid a lower rate until he passes another attentiveness test).

It should be understood that the above are merely examples of embodiments and should not be interpreted in a limiting fashion. Modifications and alterations to one or more methods described herein could be made without departing from the spirit and scope of the present invention.

Rules of Interpretation

Numerous embodiments have been described, and are presented for illustrative purposes only. The described embodiments are not intended to be limiting in any sense. The invention is widely applicable to numerous embodiments, as is readily apparent from the disclosure herein. These embodiments are described in sufficient detail to enable those skilled in the art to practice the invention, and it is to be understood that other embodiments may be utilized and that structural, logical, software, electrical and other changes may be made without departing from the scope of the present invention. Accordingly, those skilled in the art will recognize that the present invention may be practiced with various modifications and alterations. Although particular features of the present invention may be described with reference to one or more particular embodiments or figures that form a part of the present disclosure, and in which are shown, by way of illustration, specific embodiments of the invention, it should be understood that such features are not limited to usage in the one or more particular embodiments or figures with reference to which they are described. The present disclosure is thus neither a literal description of all embodiments of the invention nor a listing of features of the invention that must be present in all embodiments.

The terms "an embodiment", "embodiment", "embodiments", "the embodiment", "the embodiments", "an embodiment", "some embodiments", "an example embodiment", "at least one embodiment", "one or more embodiments" and "one embodiment" mean "one or more (but not necessarily all) embodiments of the present invention(s)" unless expressly specified otherwise. The terms "including", "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The term "comprising at least one of" followed by a listing of items does not imply that a component or sub-component from each item in the list is required. Rather, it means that one or more of the items listed may comprise the item specified. For example, if it is said "wherein A comprises at least one of: a, b and c" it is meant that (i) A may comprise a, (ii) A may comprise b, (iii) A may comprise c, (iv) A may comprise a and b, (v) A may comprise a and c, (vi) A may comprise b and c, or (vii) A may comprise a, b and c.

The terms "a", "an" and "the" mean "one or more", unless expressly specified otherwise.

The term "based on" means "based at least on", unless expressly specified otherwise.

The methods described herein (regardless of whether they are referred to as methods, processes, algorithms, calculations, and the like) inherently include one or more steps. Therefore, all references to a "step" or "steps" of such a method have antecedent basis in the mere recitation of the term 'method' or a like term. Accordingly, any reference in a claim to a 'step' or 'steps' of a method is deemed to have sufficient antecedent basis.

Headings of sections provided in this document and the title are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required, or that each of the disclosed components must communicate with every other component. On the contrary a variety of optional components are described to illustrate the wide variety of possible embodiments of the present invention.

Further, although process steps, method steps, algorithms or the like may be described in a sequential order, such processes, methods and algorithms may be configured to work in alternate orders. In other words, any sequence or order of steps that may be described in this document does not, in and of itself, indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

It will be readily apparent that the various methods and algorithms described herein may be implemented by, e.g., appropriately programmed general purpose computers and computing devices. Typically a processor (e.g., a microprocessor or controller device) will receive instructions from a memory or like storage device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media may include dynamic random access memory (DRAM), which typically constitutes the main memory. Transmission media may include coaxial cables, copper wire and fiber optics, including the wires or other pathways that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Transmission Control Protocol, Internet Protocol (TCP/IP), Wi-Fi, Bluetooth, TDMA, CDMA, and 3G.

Where databases are described, it will be understood by one of ordinary skill in the art that (i) alternative database structures to those described may be readily employed, and (ii) other memory structures besides databases may be readily employed. Any schematic illustrations and accompanying descriptions of any sample databases presented herein are illustrative arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, other formats (including relational databases, object-based models and/or distributed databases) could be used to store and manipulate the data types described herein. Likewise, object methods or behaviors of a database can be used to implement the processes of the present invention. In addition, the databases may, in a known manner, be stored locally or remotely from a device that accesses data in such a database.

For example, as an example alternative to a database structure for storing information, a hierarchical electronic file folder structure may be used. A program may then be used to access the appropriate information in an appropriate file folder in the hierarchy based on a file path named in the program.

It should also be understood that, to the extent that any term recited in the claims is referred to elsewhere in this document in a manner consistent with a single meaning, that is done for the sake of clarity only, and it is not intended that any such term be so restricted, by implication or otherwise, to that single meaning.

In a claim, a limitation of the claim which includes the phrase "means for" or the phrase "step for" means that 35 U.S.C. § 112, paragraph 6, applies to that limitation.

In a claim, a limitation of the claim which does not include the phrase "means for" or the phrase "step for" means that 35 U.S.C. § 112, paragraph 6 does not apply to that limitation, regardless of whether that limitation recites a function without recitation of structure, material or acts for performing that function. For example, in a claim, the mere use of the phrase "step of" or the phrase "steps of" in referring to one or more steps of the claim or of another claim does not mean that 35 U.S.C. § 112, paragraph 6, applies to that step(s).

With respect to a means or a step for performing a specified function in accordance with 35 U.S.C. § 112, paragraph 6, the corresponding structure, material or acts described in the specification, and equivalents thereof, may perform additional functions as well as the specified function.

Computers, processors, computing devices and like products are structures that can perform a wide variety of functions. Such products can be operable to perform a specified function by executing one or more programs, such as a program stored in a memory device of that product or in a memory device which that product accesses. Unless expressly specified otherwise, such a program need not be based on any particular algorithm, such as any particular algorithm that might be disclosed in the present application. It is well known to one of ordinary skill in the art that a specified function may be implemented via different algorithms, and any of a number of different algorithms would be a mere design choice for carrying out the specified function.

Therefore, with respect to a means or a step for performing a specified function in accordance with 35 U.S.C. § 112, paragraph 6, structure corresponding to a specified function includes any product programmed to perform the specified function. Such structure includes programmed products which perform the function, regardless of whether such product is programmed with (i) a disclosed algorithm for performing the function, (ii) an algorithm that is similar to a disclosed algorithm, or (iii) a different algorithm for performing the function.

CONCLUSION

While various embodiments have been described herein, it should be understood that the scope of the present invention is not limited to the particular embodiments explicitly described. Many other variations and embodiments would be understood by one of ordinary skill in the art upon reading the present description.

What is claimed is:

1. A method of managing a patient treatment platform, the method comprising:
   forwarding an electronic request message from the patient-treatment platform to a plurality of providers across a wide area network, the message having a prescribed plurality of standardized anatomical images related to a particular patient's medical condition configured to generate a plurality of corresponding anatomical images on one or more display devices after receipt by the plurality of providers,
   the electronic request message configured to forward the same prescribed plurality of standardized anatomical images to all the providers across the wide area network, the request message also having a plurality of possible treatment options for the particular patient's medical condition for the plurality of providers to select, the electronic request message configured to forward the same plurality of possible treatment options to each of the plurality of providers across the wide area network;
   receiving electronic response messages from the plurality of providers across the wide area network, the electronic response messages each having a selection of the plurality of possible treatment options;
   storing the selection of the plurality of possible treatment options from the electronic response messages in a database in a prescribed manner;
   accessing, as a function of the database storage structure, the selections in the database to produce an output report graphically displaying the selections from the plurality of providers;
   forwarding a faux electronic request message to at least one provider across a wide area network, the faux electronic request message having a prescribed plurality of standardized anatomical images configured to generate a plurality of corresponding anatomical images on one or more display devices after receipt by the at least one provider and at least one element of information that is incompatible with the plurality of standardized anatomical images; and
   determining the at least one provider's attentiveness based on the at least one provider's response to the faux electronic request message.

2. The method of claim 1, further comprising forwarding the output report to a treating physician of the patient.

3. The method of claim 1, wherein the plurality of standardized anatomical images includes at least one radiographic image related to the patient's medical condition.

4. The method of claim 1, wherein forwarding the electronic request message further comprises forwarding the electronic request message using IP protocols.

5. The method of claim 1, wherein the plurality of providers includes between five and fifteen providers.

6. The method of claim 1, wherein a time between forwarding the electronic request message to the plurality of providers and receiving electronic response messages from the plurality of providers does not exceed seven days.

7. The method of claim 1, wherein each provider of the plurality of providers is selected based on a propensity score stored in the database, the propensity score indicating, for a given type of medical condition, a respective provider's propensity to recommend a particular treatment option.

8. The method of claim 7, further comprising selecting the plurality of providers from a database such that an average of the propensity scores for each of the plurality of providers is within a desired range.

9. The method of claim 7, further comprising updating the propensity score for each of the plurality of providers based on the selection of the plurality of possible treatment options in each of the plurality of providers respective electronic response message stored in the database.

10. The method of claim 7, wherein each of the plurality of providers are registered with the patient treatment platform and verified based on at least one professional credential.

11. The method of claim 7, further comprising:
    forwarding the electronic request message to at least one apprentice provider, the apprentice provider failing to meet the at least one professional credential;
    receiving an electronic response message from the at least one apprentice provider, the electronic response message including a selection of the plurality of possible treatment options; and
    updating a propensity score of the at least one apprentice provider based on the selected possible treatment option in the apprentice provider's electronic response message without including the selected possible treatment option in the output report.

12. The method of claim 1, wherein the database is a relational database.

13. The method of claim 1, wherein the database includes at least one object-based model.

14. The method of claim 1, further comprising:
    authorizing, using IP protocols, a payment to a particular provider of the plurality of provider's in response to receiving the electronic response message having the selection of the plurality of possible treatment options from the particular provider.

15. The method of claim 1, wherein accessing the selections in the database further comprises determining, for each of the possible treatment options, what percentage of the plurality of providers selected the possible treatment options, and
    graphically representing the percentages in the output report.

* * * * *

UNITED STATES PATENT AND TRADEMARK OFFICE
CERTIFICATE OF CORRECTION

PATENT NO. : 10,937,552 B2
APPLICATION NO. : 16/116496
DATED : March 2, 2021
INVENTOR(S) : Zoher Ghogawala It is certified that error appears in the above-identified patent and that said Letters Patent is hereby corrected as shown below:

In the Claims

Column 34, Line 34, Claim 11, change "meet the at least one professional credential"; to "meet at least one professional credential".

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*